(12) United States Patent
Elliot

(10) Patent No.: US 10,697,050 B2
(45) Date of Patent: Jun. 30, 2020

(54) SHAPE MEMORY ACTUATOR STRUCTURES AND CONTROL THEREOF

(71) Applicant: Gibson Elliot, Fremont, CA (US)

(72) Inventor: Gibson Elliot, Fremont, CA (US)

(*) Notice: Subject to any disclaimer, the term of this patent is extended or adjusted under 35 U.S.C. 154(b) by 483 days.

(21) Appl. No.: 15/639,233

(22) Filed: Jun. 30, 2017

(65) Prior Publication Data
US 2019/0003024 A1 Jan. 3, 2019

(51) Int. Cl.
| | | |
|---|---|---|
| C22F 1/00 | (2006.01) | |
| A61B 17/00 | (2006.01) | |
| F03G 7/06 | (2006.01) | |
| A61B 17/17 | (2006.01) | |
| A61B 17/88 | (2006.01) | |

(52) U.S. Cl.
CPC .............. *C22F 1/006* (2013.01); *A61B 17/00* (2013.01); *A61B 17/17* (2013.01); *A61B 17/8866* (2013.01); *A61B 2017/00017* (2013.01); *A61B 2017/00154* (2013.01); *A61B 2017/00314* (2013.01); *A61B 2017/00867* (2013.01); *F03G 7/065* (2013.01)

(58) Field of Classification Search
CPC .................................. F03G 7/06; F03G 7/065
USPC .................................................. 60/527–529
See application file for complete search history.

(56) References Cited

U.S. PATENT DOCUMENTS

| | | | |
|---|---|---|---|
| 4,551,975 A | 11/1985 | Yamamoto et al. | |
| 4,553,393 A | 11/1985 | Ruoff | |
| 4,716,731 A | 1/1988 | Sakai et al. | |
| 6,072,154 A * | 6/2000 | Maynard | A61B 1/0058 219/209 |
| 6,133,547 A | 10/2000 | Maynard | |
| 6,408,289 B1 | 6/2002 | Daum | |
| 6,447,478 B1 | 9/2002 | Maynard | |
| 7,575,807 B1 | 8/2009 | Barvosa-Carter et al. | |
| 9,339,950 B2 | 5/2016 | Allen | |
| 2005/0275196 A1* | 12/2005 | Zanella | F03G 7/065 280/727 |
| 2006/0261709 A1 | 11/2006 | Kato et al. | |

(Continued)

OTHER PUBLICATIONS

Körner, C. and Liebold-Ribeiro, Y., "A systematic approach to identify cellular auxetic materials", Smart Materials and Structures (Dec. 19, 2014), 10 pages, vol. 24, issue 2; 025013; Copyright IOP Publishing Ltd (2015), https://www.researchgate.net/publication/269776368.

*Primary Examiner* — Laert Dounis
(74) *Attorney, Agent, or Firm* — Blue Filament Law PLLC

(57) ABSTRACT

A shape memory actuator system and control methods thereof are provided that include a shape memory actuator having a body made of shape memory material, with individual power conductors interfaced with a first portion of the body, and one or more individual ground conductors interfaced with a second portion of the body. A power source provides power to the individual power conductors. One or more controllers are provided for pulse controlling or regionally controlling a resistive heating current connection sufficient to impart shape memory to the body or regions of the body between the individual power conductors and the one or more individual ground conductors with the provision that the ground conductors are physically separated from the individual power conductors. Structures of shape memory actuators and methods of control are also provided.

29 Claims, 17 Drawing Sheets

(56) References Cited

U.S. PATENT DOCUMENTS

2007/0120444 A1  5/2007  Kato et al.
2017/0191470 A1  7/2017  Elliot

* cited by examiner

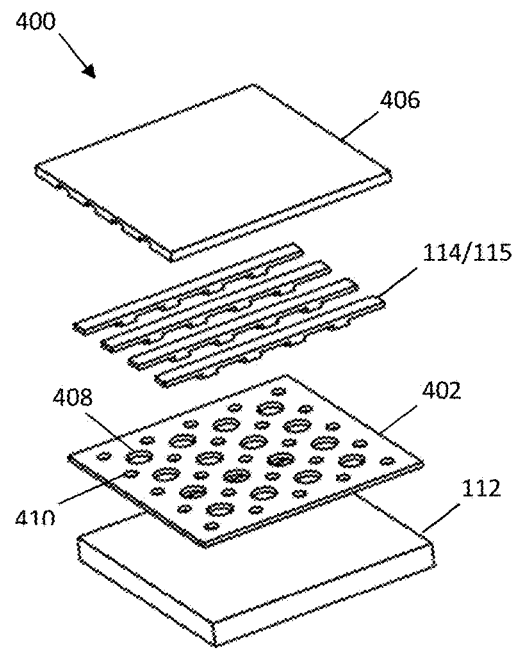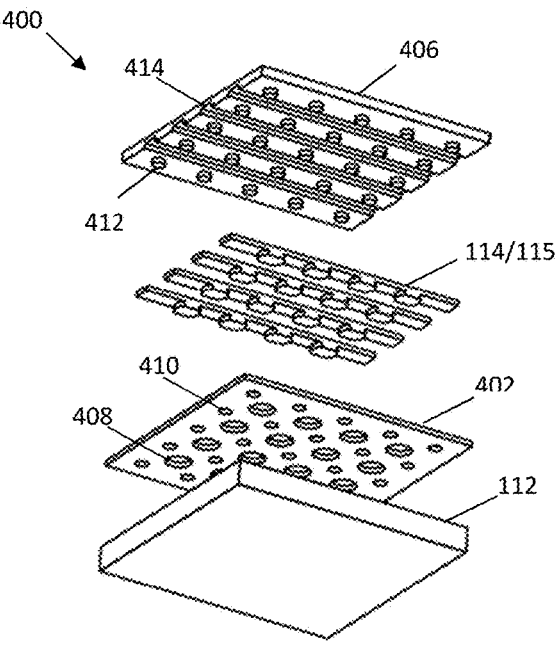
FIG. 12A
FIG. 12B
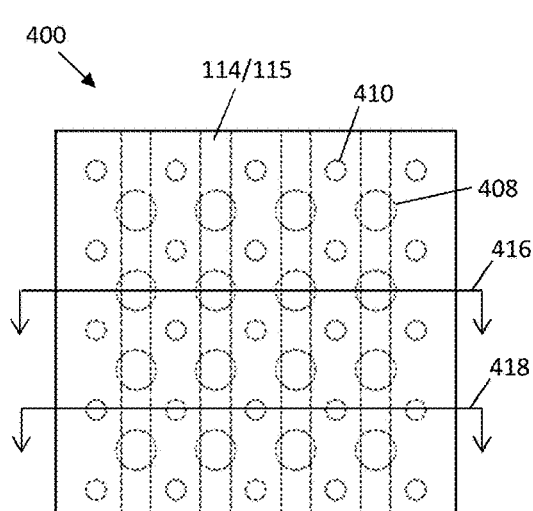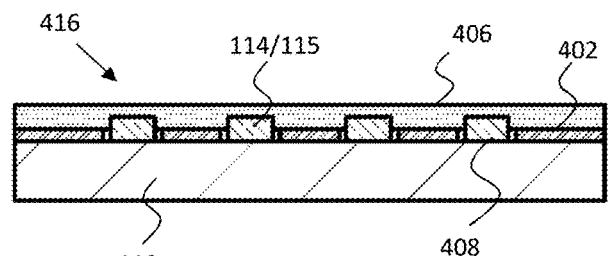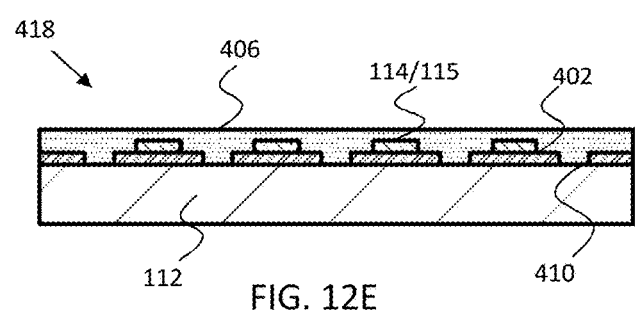
FIG. 12C
FIG. 12D
FIG. 12E

SHAPE MEMORY ACTUATOR STRUCTURES AND CONTROL THEREOF

TECHNICAL FIELD

The present invention generally relates to shape memory actuators, and in particular to the structure and control thereof.

BACKGROUND

Nitinol and similar shape memory materials (SMM) have unique material properties, which allow them to be pre-formed in a desired "memorized" shape and return to that shape after any deformation above a material specific phase-change temperature. When a heat source is removed and the temperature drops below the phase-change temperature, the shape memory material retains a deformable state. The temperature range for controlling the shape may be varied based on the composition of the SMM and the techniques used to process and form the SMM. Due to the ability to control the shape of such a flexible, yet strong material has led to a variety of applicable uses for SMM.

However, the traditional methods for constructing and controlling a SMM, or actuators that are embedded with SMMs, has been limited for several reasons. SMMs are slow to reach the disparate temperatures required for transition without outside intervention. The SMM typically requires a cooling source to reduce the temperature of the material after being driven to the opposite phase to allow for transition back to the deformable state. To obtain the required temperature change, the materials are typically constructed with individual shape memory elements connected at their ends in much the same way a traditional wire wound resistor is constructed. However, these constructions formed with individual SMM elements have very limited geometries and require complex multipart mountings. Furthermore, the constant flexing of the SMM causes the mechanical connections between individual SMM elements to fatigue and rapidly fail overtime, which reduce the overall durability and longevity of these actuators, greatly increasing replacement and maintenance costs.

In addition, traditional methods to control multiple mechanical axis and multiple degrees of freedom of the actuators with SMMs have resorted to using individual conductors to heat each individual SMM element. The more SMM elements to drive the actuator, the more wiring that is required, which results in a larger size actuator, higher costs, reduced durability, and can lead to undesired thermal management design considerations. As such, the current actuators and designs have resulted in poor performance and their control has been limited to only one or two degrees of freedom. Having only one to two degrees of freedom of control greatly limits the use of SMM for a variety of applications.

The limited control of a unitary, monolithic structure of SMM to form a shape memory actuator (SMA) has also been described in the literature, such as the SMA described in U.S. Pat. No. 4,551,975. The disclosed SMA includes a plurality of separated conductors interfaced with a surface of SMM. A controller forms circuits between two or more specific conductors to control a path of current in SMM situated between those specific conductors to heat and activate those sections of SMM. However, the configuration of this SMA has limited control resolution, among other drawbacks. In general, a higher degree and resolution of control of particular sections of a unitary, monolithic SMA requires additional conductors and conduction points to heat specific sections of the SMM. As the density of conductors increase, the signal pathways for control (i.e., the controller leads directing the current) also need to increase, where the number and availability of signal pathways may become a limiting factor affecting the potential control resolution of the SMM.

Thus, there is a need in the art for new structural designs of shape memory actuators and methods of control thereof to improve the overall versatility, agility, and control resolution of SMAs. There is a further need to control an actuator or SMM in multiple axes and in multiple degrees of freedom to greatly expand their applicable uses.

SUMMARY OF THE INVENTION

A shape memory actuator system is provided that includes a shape memory actuator having a body made of shape memory material, with a plurality of individual power conductor interfaced with a first portion of the body, and one or more individual ground conductors interfaced with a second portion of the body. A power source provides power to the plurality of individual power conductors. A pulse controller is provided to control a frequency of current pulses sufficient to impart a step-wise shape memory effect to the body between the one or more of the plurality of individual power conductors and the one or more individual ground conductors with the proviso that the one or more individual ground conductors are physically separated from the plurality of individual power conductors.

A shape memory actuator system is provided that includes a shape memory actuator having a body made of a shape memory material partitioned into two or more control regions, each control region having a plurality of individual power conductors interfaced with a first portion of the control region, and one or more individual ground conductors interfaced with a second portion of the control region. A power source provides power to the plurality of individual power conductors. A plurality of region controllers are provided where each region controller is positioned in each control region for controlling a resistive heating current connection within each control region sufficient to impart shape memory between the one or more of the plurality of individual power conductors and the one or more individual ground conductors with the proviso that the one or more individual ground conductors are physically separated from the plurality of individual power conductors.

A layered shape memory actuator is provided that includes an SMM body, an insulation layer, a plurality of conductors, and a sealant layer. The insulation layer is configured to provide insulation and reduce cross-talk between conduction points and has a series of conduction holes and a series of sealant holes, where the conduction holes permit portions of the conductors to interface directly with the SMM body at desired conduction points, or sections, and the sealant holes are configured to permit a sealant to interface and anchor directly to the SMM body to ensure the sealant layer, the conductors, the insulation layer, and the SMM body are securely assembled together.

An auxetic shape memory actuator is provided configured to form three-dimensional (3-D) shapes starting from a 2-D planar structure or sheet formed from an SMM body having an auxetic internal structure. The auxetic shape memory actuator includes a plurality of individual power conductors interfaced with a first portion of the SMM body, and one or more individual ground conductors interfaced with a second portion of the SMM body. A power source provides power to the plurality of individual power conductors. A controller is provided for controlling a resistive heating current connection sufficient to impart shape memory between the one or more of the plurality of individual power conductors and the one or more individual ground conductors with the proviso that the one or more individual ground conductors are physically separated from the plurality of individual power conductors

BRIEF DESCRIPTION OF THE DRAWINGS

The present invention is further detailed with respect to the following drawings that are intended to show certain aspects of the present of invention, but should not be construed as limit on the practice of the invention. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale.

FIG. 4B is a perspective view of the controller and FIG. 4C is a side view thereof;

FIG. 5A is a perspective view thereof and FIG. 5B is a cross-section view thereof;

FIG. 6A is a front view thereof, and FIG. 6B is a top view thereof;

FIG. 7A depicts the actuator in an unactuated state, and FIG. 7B depicts a portion of the in-line actuators in an actuated state;

FIG. 9A is a perspective view of one actuator, FIG. 9B a front view of two actuators to be connected, FIG. 9C is a longitudinal cross-section view of the two actuators, and FIG. 9D is a detailed view of the circled region shown in FIG. 9C;

FIG. 10A is a perspective view of two actuators connected, FIG. 10B is a cross-section view of the actuators along the line shown in FIG. 10A, and FIG. 10C is a detailed view of the circled region shown in FIG. 10B;

FIG. 11A is perspective view thereof, FIG. 11B is a front view of an angular section thereof, FIG. 11C is a side view of the angular section thereof, and FIG. 11D is front view of a larger angular section thereof;

FIGS. 12A-12E illustrate a system and method for assembling or manufacturing a shape memory actuator in accordance with embodiments of the invention, where FIG. 12A is an exploded top perspective view thereof, FIG. 12B is an exploded bottom perspective view thereof, FIG. 12C is an assembled top view thereof shown with hidden lines, FIG. 12D is a cross section view thereof taken along a first line shown in FIG. 12C, and FIG. 12E is a cross section view thereof taken along a second line shown in FIG. 12C;

FIG. 13A depicts the actuator in an unactuated state, and FIG. 13B depicts the actuator in an actuated state;

FIG. 14A depicts the actuator in an unactuated state, and FIG. 14B depicts the actuator in an actuated state; FIG. 15A is a front view of the actuator, and FIG. 15B is back view thereof.

DETAILED DESCRIPTION

Figure 1A:
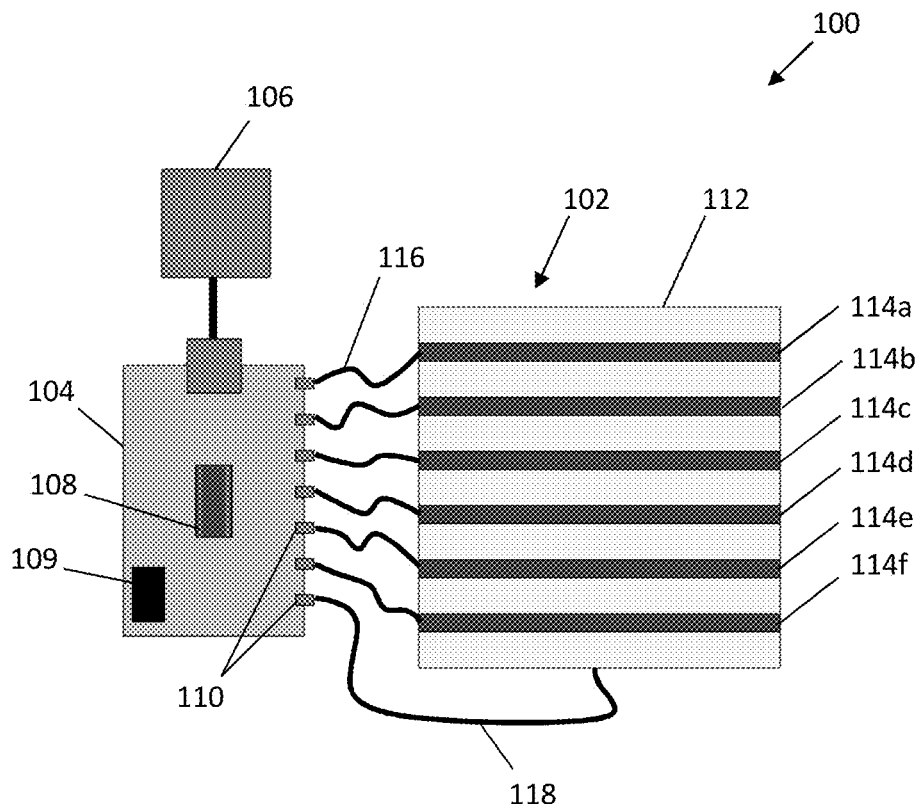
FIG. 1A illustrates a prior art shape memory actuator system per co-pending application U.S. Ser. No. 14/988,266.

The present invention has utility as a system and method for the remote, semiautonomous, or autonomous control of particular shape memory actuator (SMA) structures for their use in multiple applications. In particular, the system and method has utility in robotics and medical applications including the delivery of therapeutics, safely navigating arteries and veins, steering a surgical cutter, and aligning bony fractures. It should be appreciated that as embodiments of the invention are directed to robotic and medical applications, the system and methods may also be used in other fields such as mining, oil and gas exploration, buildings and structures, communications, and optics.

The following description of various embodiments of the invention is not intended to limit the invention to these specific embodiments, but rather enable any person skilled in the art to make and use this invention through exemplary aspects thereof.

It is to be understood that in instances where a range of values are provided that the range is intended to encompass not only the end point values of the range cut also intermediate values of the range as explicitly being including within the range and varying by the last significant figure of the range. By way of example, a recited range from 1 to 4 is intended to include 1-2, 1-3, 2-4, 3-4, and 1-4.

As used herein, a shape memory material (SMM) may be considered synonymous with shape memory alloys, smart metals, memory metals, memory alloys, or smart alloys. The general attribute of a SMM is the property of having two or more states; at least one "memorized" state, and a deformable state. The SMM, or particular sections/regions of the SMM, are pre-treated to one or more desired "memorized" states and retains the "memorized" states when one or more phase change temperature(s) are reached. The phase change temperature(s) can vary and be tailored to a particular temperature range depending on the methods of manufacture and composition of the materials. Any material or alloy exhibiting this general property may be considered a SMM illustratively including, but not limited to, nickel-titanium (Nitinol), copper-aluminum-nickel, copper-zinc-aluminum-nickel, copper-zinc, iron-platinum, silver-cadmium, and combinations thereof.

Also used herein are the terms "power conductors" and "ground conductors". In general, a conductor refers to an object or type of material that permits the flow of electric current. A power conductor refers to a conductor that directly receives power from a power source. A ground conductor refers to a conductor that receives power from the power conductor. However, it should be appreciated that the described locations of power conductors and ground conductors may be interchangeable, and are merely defined separately to aid in understanding embodiments of the invention. As specific types of conductors are referenced herein, typical conductors that may be used illustratively include graphene, copper, stainless steel, aluminum, other conductive metals and metal alloys, conductive coatings, and equivalents thereof.

Embodiments of the present invention generally describe a shape memory actuator, and a system and method for controlling the shape memory actuator. By controlling the temperature at specific sections on a SMM, only those specific sections are activated to their "memorized" state. Depending on the shape and design of the shape memory actuator(s), a plurality of configurations and movements may be controlled.

Figure 1B:
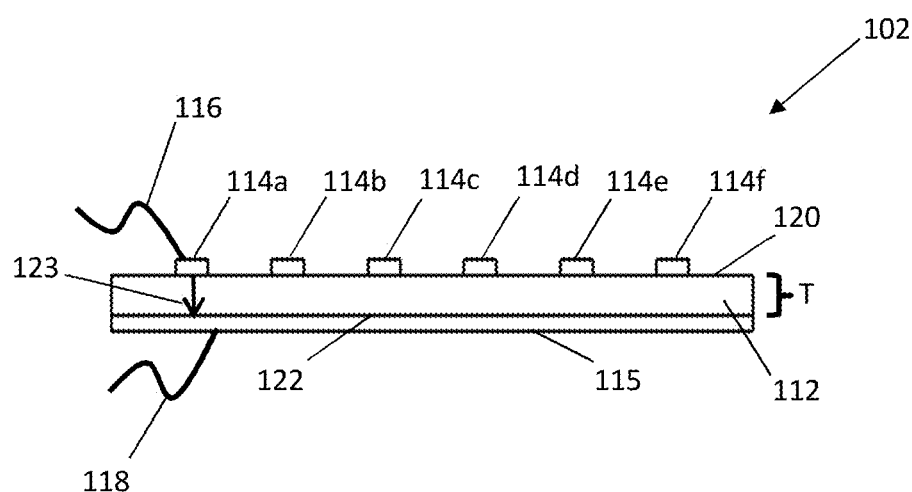
FIG. 1B illustrates a prior art view of a set of general components of a shape memory actuator attached to the system per co-pending application U.S. Ser. No. 14/988,266.

With reference to the figures, FIG. 1A-1B illustrates a shape memory actuator system 100, which is described in more detail in co-pending application U.S. Ser. No. 14/988,266 incorporated by reference herein in its entirety. The system 100 generally includes a shape memory actuator 102, a controller 104, and a power source 106. The shape memory actuator 102 generally includes a body 112 made of shape memory material (SMM) and a plurality of individual conductors (114a-114f, 115) at least partially interfaced with portions of the body 112. The controller 104 generally includes a microprocessor 108, memory (e.g., RAM, ROM) 109, and a series of ports 110 and/or controller leads (116, 118) to electrically connect the controller 104 with the plurality of individual conductors (114a-114f, 115). The controller leads (116, 118), as used herein, refer to wires, I/O pins, or other conductive substance that electrically connects the conductors (114a-114f, 115) with the communications from the controller 104. Other peripherals known in the art may also be in communication with the controller 104 illustratively include a user-interface, user-input mechanisms (e.g., keyboard, mouse), additional memory storage, and data input mechanisms (e.g., optical disc reader, compact disc (CD) reader, universal serial bus (USB) interface). In a particular embodiment, the controller 104 may be a computer containing specific software, data, and utilities to allow a user to manually control and/or develop software to control the shape memory actuator 102. The controller 104 is configured to activate specific sections, or points, of the SMM by controlling the formation of one or more circuits and current flow between: i.) at least one individual power conductor 114a-114f; ii.) at least one ground conductor 115; and iii.) a section or point, of the SMM body 112 situated between the at least one power conductor 114a-114f and the at least one ground conductor 115.

The controller 104 receives power from a power source 106. The power source 106 may be for example, one or more batteries, a connection to an electrical outlet, an electromagnetic power induction coil, other forms of wireless power transfer, one or more solar cells, a thermal power inductor, a microwave, and equivalents thereof. In a specific embodiment, the controller 104 and power source 106 is an individual unit with loaded software, data, utilities, or other executables to autonomously control the shape memory actuator 102 without user assistance.

As best shown in FIG. 1B, in which like reference numerals have the meaning ascribe to that numeral with respect to the aforementioned FIG. 1A, the shape memory actuator 102 includes a plurality of individual power conductors depicted as 114a-114f at least partially interfaced with a first portion of the body 112, and one or more individual ground conductors 115 at least partially interfaced with at least a second portion of the body 112. The power conductors 114a-114f and the one or more ground conductor(s) 115 are physically separated to create a section, or point, of shape memory material therebetween. For example, as shown in FIG. 1B, the individual power conductors 114a-114f are interfaced on a first surface 120 of the body 112 (defining a first portion of the body 112) and the ground conductor 115 is interfaced with a second surface 122 of the body 112 (defining a second portion of the body 112). Therefore, the power conductors 114a-114f and ground conductor 115 are physically separated by the thickness T of the body 112.

Each individual power conductor 114a-114f has a power electrical connection 116 to a port 110 or power lead 116 of the controller 104. Likewise, each ground conductor 115 has a ground electrical connection or ground lead 118 to a port 110 of the controller 104. It is appreciated that two or more of the ground conductors 115 can share a single port 110 so as to act in concert. The controller 104 can therefore control the connections/disconnections between:
   a. one or more of the individual power conductors;
   b. one or more of the ground conductor(s); and
   c. a section, or point, of the SMM body situated between
      a. and b.

The controller in some inventive embodiments, controls how (e.g., steady state, modulated) and/or the amount of current driven through the created connection(s), where the current follows the least path of resistance through the shape memory material between the connection(s). For example, the controller 104 may create a connection and send current between individual power conductor 114a and the ground conductor 115. The current would therefore flow through the thickness T of the material between this connection as shown by arrow 123 which depicts the flow of current through the specific section, or point, of the SMM body 112 between conductors 114a and 115. This causes the SMM to heat at this section through a phenomenon known synonymously as ohmic heating or resistive heating. Once this area reaches the phase change temperature, the area conforms to the "memorized" state. The controller in some inventive embodiments, modulates the current flowing through the power conductor 114a and ground conductor 115 to maintain the heat of the material at or near the phase-change temperature. Once the temperature drops below the phase change temperature, the actuator 102 may be deformed to a previous configuration using an external mechanism. External mechanisms operative herein illustratively include a spring, a compressive die, an elastic coupler, a pulley, a motor and gears, a piston, or a combination of any of the aforementioned. Using these general principles of the shape memory actuator system 100, various embodiments of the shape memory actuator 102 can be controlled, which are further described in detail below.

Parallel Array of Power and Ground Conductors

Figure 2A:
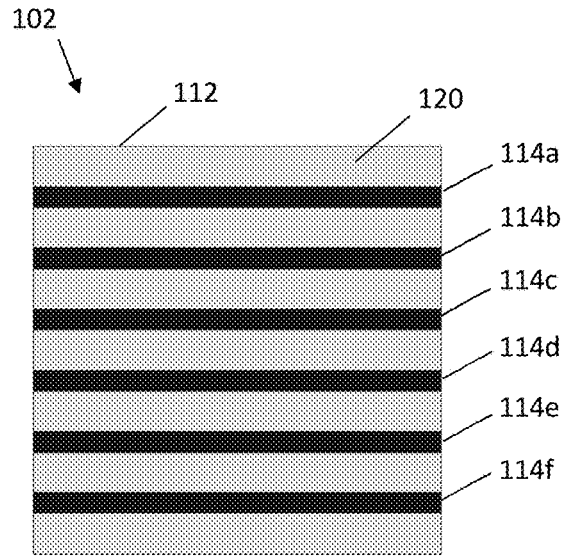
FIGS. 2A-2C illustrate prior art views of a controllable shape memory actuator with a parallel array of a plurality of individual power conductors interfaced on a first surface (FIG. 2A), a parallel array of a plurality of individual ground conductors interfaced on a second surface (FIG. 2B), and a transparent view of the actuator showing a plurality of conduction points created by the intersection of the two parallel arrays (FIG. 2C) per co-pending application U.S. Ser. No. 14/988,266.
Figure 2B:
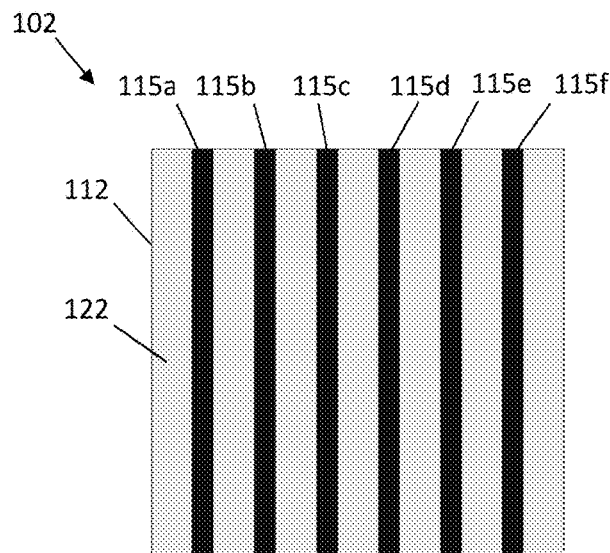
Figure 2C:
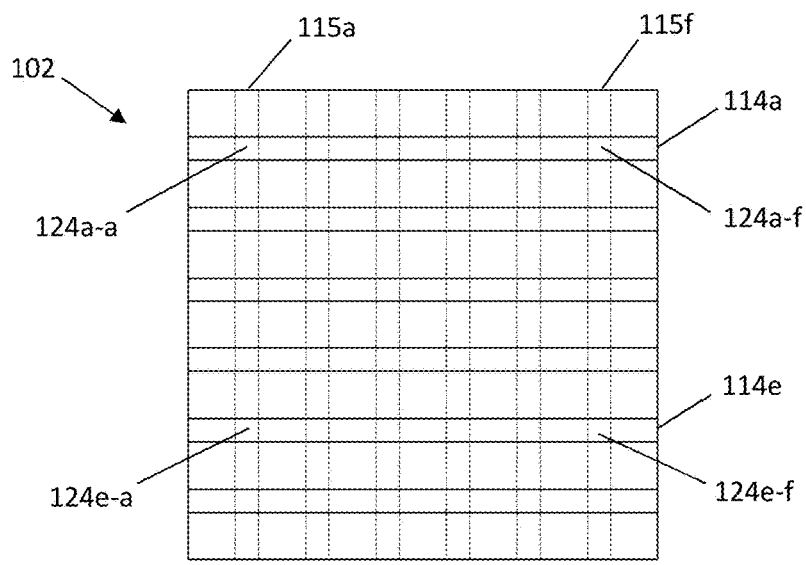

With reference to FIGS. 2A-2C, in which like reference numerals have the meaning ascribe to that numeral with respect to the aforementioned drawings, in a particular embodiment, the shape memory actuator 102 includes a parallel array of a plurality of individual power conductors 114a-114f on a first surface 120 of the body 112 (FIG. 2A) and a parallel array of a plurality of individual ground conductors 115a-115f on a second surface 122 of the body 112 (FIG. 2B), where the orientation of the parallel array of power conductors 114a-114f is non-parallel and intersecting with respect to the orientation of the parallel array of ground conductors 115a-115f. This is best shown in FIG. 2C, where the dotted lines represent the outline of the individual ground conductors 115a-115f on the second surface 122 of the body 112 and the solid lines represent the outline of the individual power conductors 114a-114f on the first surface 120 of the body 112. The power conductors 114a-114f and ground conductors 115a-115f are physically separated by the thickness of the body 112. It should be appreciated that while the array of conductors 114a-114f and 115a-115f are depicted as orthogonal in FIGS. 2A-2C, the angle of intersection between an individual power conductor and an individual ground conductor can assume any angle to define a desired ohmic heating in a shape change material therebetween. In addition, the number of individual power conductors 114 and ground conductors 115 may vary depending on a user's preference and application as further described below.

The orientation of the power conductors 114a-114f with respect to the ground conductors 115a-115f creates an array of conduction volumes (124a-a thru 124e-f) as shown in FIG. 2C. Conduction volumes are also referred to herein as conduction points. The array of conduction points 124 provides specific sections or regions where the SMM can be activated and controlled. For instance, if the controller 104 creates a connection and provides current between power conductor 114a and ground conductor 115a, then current flows through conduction point 124a-a and heats only this section of the body 112 (the section here being the location of conduction point 124a-a). If the controller 104 creates a connection and provides current between power conductor 114e and ground conductor 115f, then current flows through conduction point 124e-f, likewise only heating this section of the body. The controller 104 may therefore heat one or more specific sections of the SMM body 112 at one or more conduction points 124, resulting in a plurality of controllable configurations. It is noted, that different sections of the SMM in some inventive embodiments, are treated to have different 'memorized' configurations. For example, the body 112 at conduction point 124a-a may have a memorized state that bends into the page, while the body 112 at conduction point 124e-f may have a memorized state that bends out of the page.

Figure 2D:
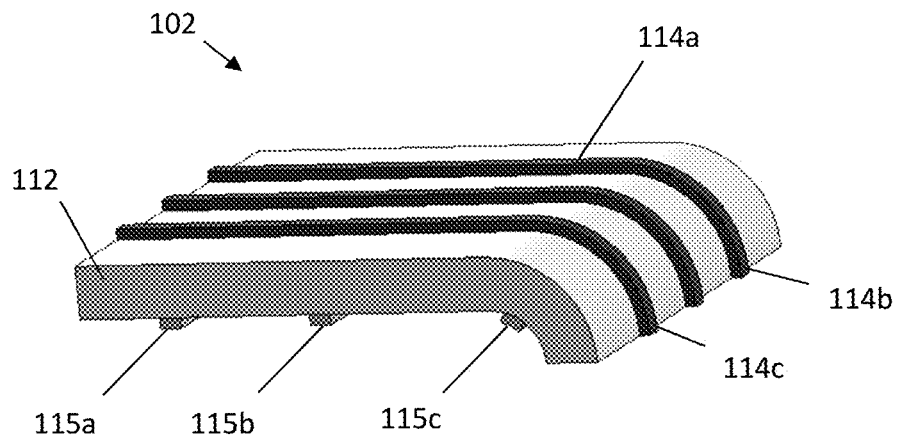
FIGS. 2D and 2E depict prior art examples of different configurations of the controllable shape memory actuator per co-pending application U.S. Ser. No. 14/988,266.

For example, with reference to FIG. 2D, in which like reference numerals have the meaning ascribe to that numeral with respect to the aforementioned drawings, if the controller 104 creates a connection and provides power between power conductors 114a, 114b and 114c, and ground conductor 115c, a bend may result in the actuator 102 (depending on the pre-treatment of the SMM) at this region due to the heating at conduction points 124a-c, 124b-c, and 124c-c. The controller 104 may create an additional connection with ground conductor 115b, causing the actuator 102 to bend even further.

Figure 2E:
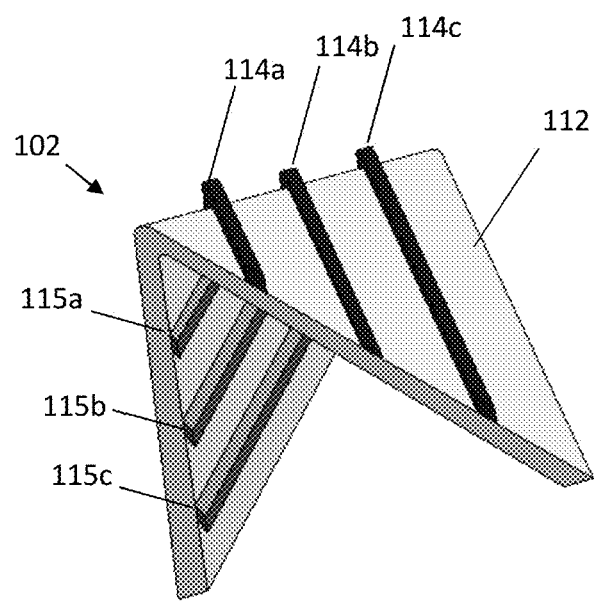

In another example, with reference to FIG. 2E, in which like reference numerals have the meaning ascribe to that numeral with respect to the aforementioned drawing, the controller 104 may cycle through various connections, or cycle the current through the connections to create a bend across the diagonal of the actuator 102. If the controller 104 cycles through conductor's 114a-115a, 114b-115b and 114c-115c, the diagonal of the actuator 102 heats, causing the configuration as shown in FIG. 2E. As a result, through a programmed sequence of iterative heatings through controller 104 dynamically adjusting time, current flow, and sequence of specific conductors 114a-114f, a wide variety of material shapes can be imparted to a memory state for the material. In the example shown in FIGS. 2D and 2E the SMM was pre-processed with a "memorized" state having a bend across the body 112.

The particular advantage of forming a plurality of conduction points on the SMM body 112 is the dramatic increase in the control resolution. Very specific points of the SMM body 112 can be activated by forming a circuit between just one power conductor and one ground conductor.

Methods of Control—Pulse Control

Figure 3A:
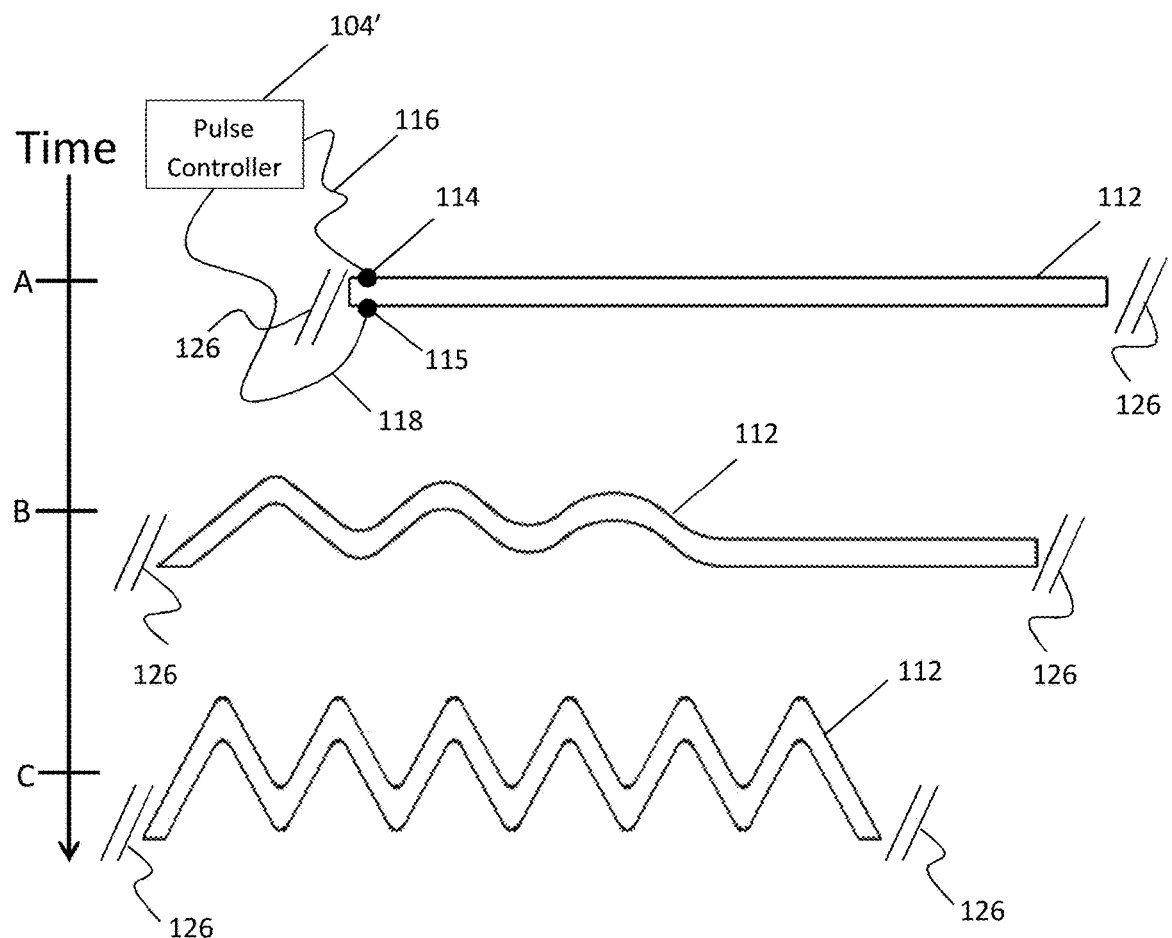
FIG. 3A illustrates a first method of pulse control for controlling a shape memory actuator in accordance with embodiments of the invention.

In a particular inventive embodiment, with reference to FIG. 3A, a system and method for pulse controlling an SMM body 112 is shown. The pulse controlled SMM body 112 is shown in various controllable configurations as a function of time, where the top diagram at time point A shows a specific section of the SMM body 112 in a deformable state, the middle diagram at time point B shows the specific section of the SMM body 112 in a partially 'memorized' state, and the bottom diagram at time point C shows the specific section of the SMM body 112 in a fully 'memorized' state. The pulse controlled SMM body 112 generally includes a pulse controller 104' for controlling a frequency of electrical current pulses, a power conductor 114 interfaced with a top surface of the SMM body 112 and connected to the controller 104' by a power wire 116, and a ground conductor 115 interfaced with a bottom surface of the SMM body 112 and connected to the controller 104' by a ground wire 118. For clarity and conciseness, two diagonal lines 126 are shown at the ends of the SMM body 112 so as to show an example of a specific section of the SMM body 112 that is pulse controlled. The SMM body 112 in some inventive embodiments, extends beyond these diagonal lines 126 and have different pulse controlled sections by different sets of power conductors 114 and ground conductors 115.

Pulse control of a specific section of the SMM body 112 may be performed in the following manner for a specific inventive embodiment. The specific section (e.g., the section between diagonal lines 126) may be controlled by emitting a pulse of electric current on the order of milliseconds (depending on the thickness of the SMM body, the amount of current/voltage/resistance, and mass) to achieve a partial actuation (as shown at time point B). In the generally accepted state of the art, SMMs have been controlled on and on-off or binary manner. Embodiments of the inventive pulse control method allow for partial and/or incremental actuation of a specific section of the SMM body 112 through partial incremental ohmic heating. At play is the variability of resistance of the SMM as well as heat propagation. As each pulse of electric current is delivered, as observed in direct experimental tests, a portion of the specific section of the SMM body 112 is activated. Multiple sequential pulses over time results in a stepped activation of that specific section of the SMM body 112 as can be seen by the progressive activation of the SMM body 112 from time point A to time point C. The benefit of pulse control is that the pulse control allows for further resolution of control over specific sections of the SMM body 112 without the need for additional physical trace matrix pitch and density (i.e., the need to increase the density of individual conductors (114, 115) interfaced with a specific section of the SMM body 112).

Figure 3B:
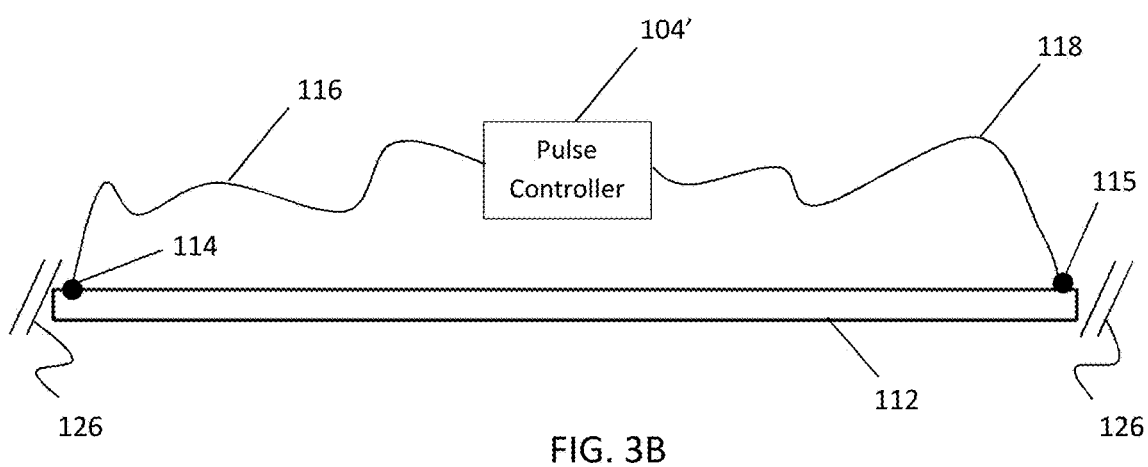
FIG. 3B illustrates a second method of pulse control for controlling a shape memory actuator in accordance with embodiments of the invention.

FIG. 3B is an embodiment of a pulse controlled SMM body 112 having the power conductor 114 interfaced on one end of a section of the SMM body 112 and a ground conductor 115 interfaced on an opposing end of a section of the SMM body 112. FIG. 3B illustrates an embodiment where the power conductor 114 and ground conductor 115 may be separated by the length of a pulse controlled section. The partial and time dependent activation of the SMM body 112 shown in FIG. 3B may be controlled and behave in a similar manner as that of the SMM body 112 shown in FIG. 3A. However, having the power conductor 114 and ground conductor 115 separated by the length of a pulse controlled section of the SMM body 112 may cause the section to actuate more uniformly from both ends, rather than from one end as depicted in FIG. 3A.

Methods of Control—Frequency Domain Control Over Specific Region Controllers

Figure 4A:
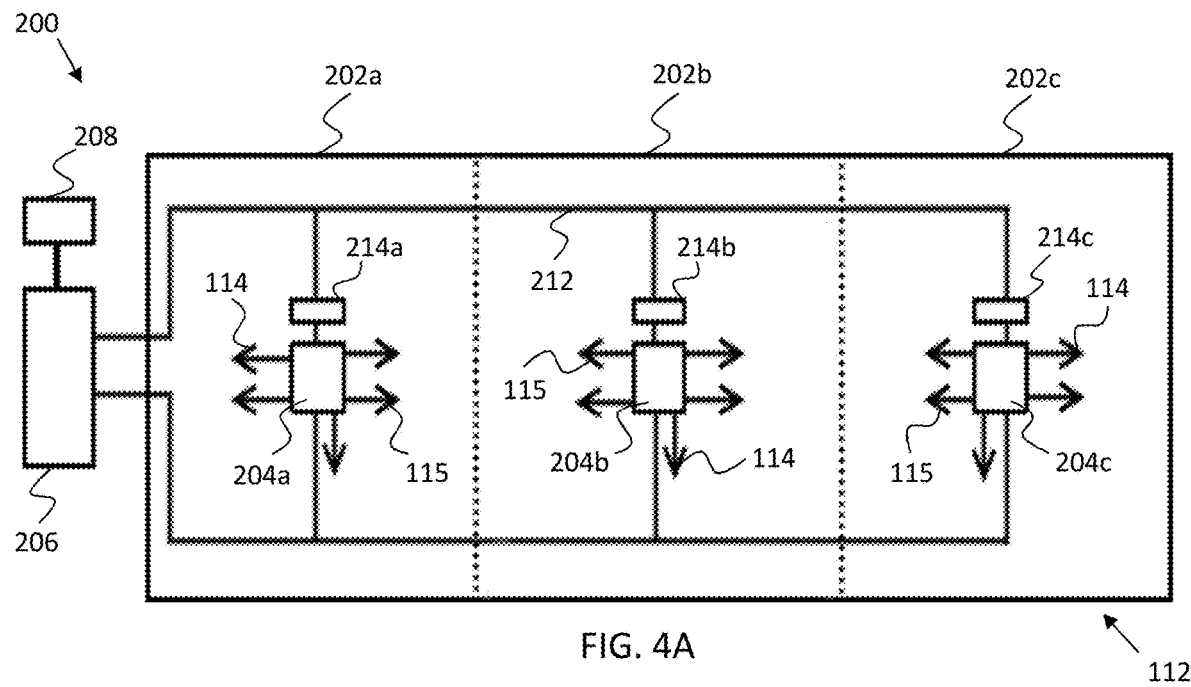
FIG. 4A illustrates a broadband control actuator system for controlling specific regions of shape memory in accordance with embodiments of the invention.

In specific inventive embodiments, with reference to FIG. 4A, a broadband control system actuator 200 is shown for improving the control resolution of specific regions of a SMM. The problem is, as higher density matrices (i.e., higher number of conductors interfaced with the SMM) require additional signal pathways for control (i.e., additional number of controller leads/contacts from a controller), the direct relationship between control communications and actuation arrays (i.e., regions of SMM to be actuated) can limit potential resolution of possible SMM actuations. Thus, the control resolution of a particular region of SMM may be limited by the number of signal pathways the controller can create or generate. Embodiments of the broadband control system are configured to improve the control resolution of different regions of an SMM to overcome the aforementioned problem.

Figure 4B:
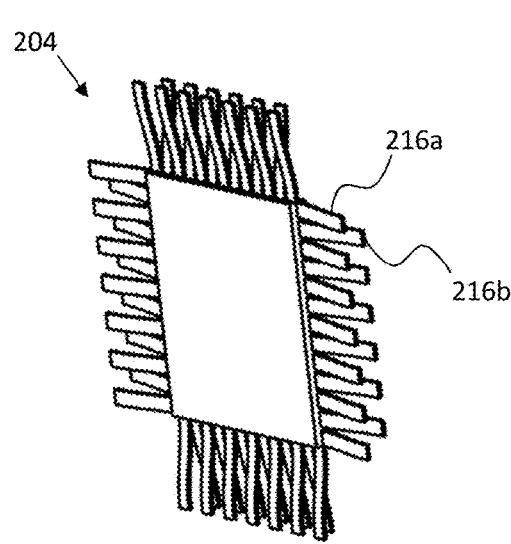
FIGS. 4B and 4C illustrate a controller having alternating leads in accordance with embodiments of the invention, where
Figure 4C:
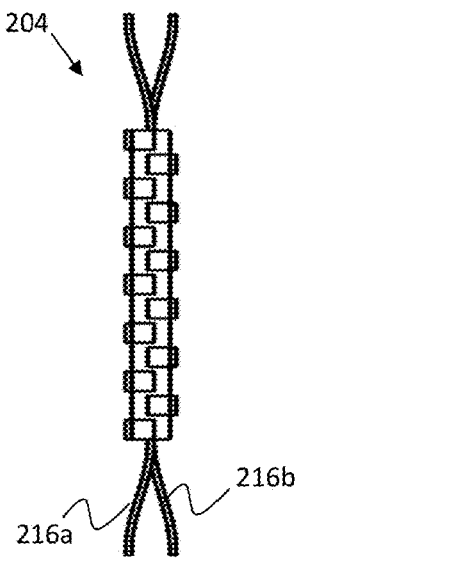

The broadband control actuator system 200 includes an SMM body 112 broken up into a plurality of SMM control regions (202a, 202b, 202c), also referred to as control 'islands', illustratively demarcated by the dotted lines shown in FIG. 4A. In a particular inventive embodiment, all of the control regions (202a, 2022b, 202c) exist on a monolithic SMM body 112 and are merely differentiated from one another by the regions that they control. Each control region (202a, 202b, 202c) includes a region controller (204a, 204b, 204c) configured to select and control the activation of specific sections of the SMM body 112 within their corresponding control region (202a, 202b, 202c). Each region controller (204a, 204b, 204c) is in electrical communication with their own sets of power conductors 114 and ground conductors 115 to control this activation using the ohmic heating methods as described above. It should be appreciated that the conductors (114, 115) are illustrated as bold arrows in FIG. 4A so as to not clutter the figure, where in reality, the conductors (114, 115) are traced on the SMM body 112 within their control regions (202a, 202b, 202c) similar to that as shown and described in FIGS. 1A-2E, as well as any other conductor tracing configurations described in U.S. patent application Ser. No. 14/988,266. The region controllers (204a, 204b, 204c) may be attached/connected/integrated to the SMM body 112 by several methods. In one method, the region controllers (204a, 204b, 204c) may be mounted directly on the surface of the SMM body with fastening elements (e.g., screws, nuts, bolts, clasps, clamps), adhesives, or I/O pin connections that make direct contact with conductors (114, 115) already traced on the SMM body 112. In a specific embodiment, the region controllers (204a, 204b, 204c) may be embedded within the SMM body 112, or fit within a piece of removed SMM from the SMM body 112, to permit the controller leads to interface with a top surface and bottom surface of the SMM body 112. For example, in a particular inventive embodiment, with reference to FIGS. 4A-4B, a region controller 204 is shown having alternating leads (216a, 216b), which are configured to interface with two separate portions (e.g., surfaces) of an SMM body 112 by fashioning the leads (216a, 216b) in an alternating configuration. For example, a first lead 216a is bent in a first direction, while an adjacent lead 216b is bent in an opposing direction. Thus, the leads may quickly align with conductors (114, 115) interfaced in a similar configuration on a top surface and a bottom surface of the SMM body 112.

The broadband control system 200 may further include a master controller 206 connected to a power source 208. The master controller 206 is configured to send a multichannel parallel signal over a common medium such as the SMM body 112, a ground plane, a power plane, or other wired connection 212 to the region controllers (204a, 204b, 204c) to coordinate actuations and/or movements of the SMM body 112 as a whole or at least part of a whole (e.g., actuations that span over several control regions (202a, 202b, 202c) or particular combinations of control regions (202a, 202b, 202c)). Each region controller (204a, 204b, 204c) may be outfitted with either one or more discreet hardware notch filters (214a, 214b, 214c) or a software notch filter that enables each region controller (204a, 204b, 204c) to discriminate, filter, and process signals for each region controller (204a, 204b, 204c). The master controller 206 may then send a single as a multichannel parallel signal through the common medium where each filter (214a, 214b, 214c) is tuned to one or more specific channels to read specific actuation commands within from the single multichannel signal. This allows for parallel operation of a multitude of control regions (202a, 202b, 202c) thus minimizing the requirement for individual signaling pathways to each region controller (204a, 204b, 204c) that would otherwise be required.

The multichannel signal may be embedded in a power line, following, for example, the X10 industry standard protocol, to provide both power and control commands to each region controller (204a, 204b, 204c). The multichannel signal may use other signaling protocols including a custom protocol or an Ethernet protocol. The multichannel signal may be modulated and/or multiplexed using techniques known in the art. The hardware filters (214a, 214b, 214c) and/or software filters may include: TEO filters; demodulators; demultiplexers; low-pass, high-pass filter, or band-pass filters; other passive, active or digital filters; and combinations thereof. It should be appreciated, that the master controller 206 and control regions (204a, 204b, 204c) may be interconnected by traditional serial or parallel digital communications. The control method above does not preclude the use of such traditional mechanisms for creation of a control level network, but may be used as an augmented, as well as a stand-alone scheme. In a specific embodiment, an optically transparent coating may be used for communications, somewhat similar to a store sign made of plastic having light piping to enhance appearance. The SMM body 112 may be coated with a transparent coating to act as a light pipe, and as such the TEO filter concept may work as an alternative to communications over power. In addition, the communications through the transparent coating provides an appealing visual effect when in operation.

Figure 4D:
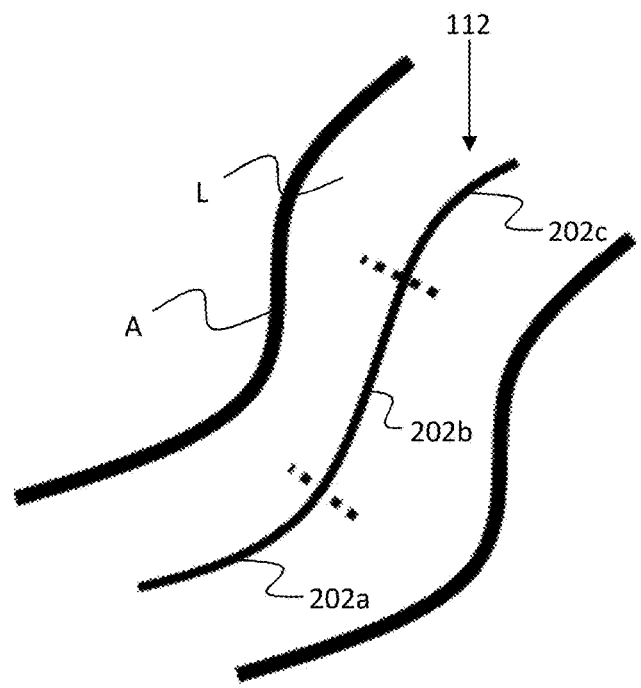
FIG. 4D is an applicable example of the broadband control actuator system in accordance with embodiments of the invention.

The broadband control actuator system 200 is particularly advantageous for improving control resolution especially when a high-level of control is needed to achieve a particular objective. For example, with reference to FIG. 4D, an SMM body 112, such as a catheter for drug delivery, having several control regions (202a, 202b, 202c) is shown traversing through a narrow bend within a lumen L of an artery A. The master controller 206 may be in communication with an electromagnetic tracking system and/or real-time x-rays/fluoroscopy that provides positional information of the SMM body 112 relative to the anatomy. The master controller 206 further knows the geometry and location of each control region (202a, 202b, 202c) with respect to one another. With this information, the master controller 206 may send a multichannel signal through a single parallel-wired connection 212, where each signal within the multichannel signal targets a specific control region (202a, 202b, 202c). The filters (214a, 214b, 214c) filter their specific signal to cause the region controller (204a, 204b, 204c) to activate and/or configure specific sections of their control region (202a, 202b, 202c), respectively, to conform to the shape of the artery. Therefore, as the SMM body 112 is pushed through the lumen L, each control region (202a, 202b, 202c) may continually actuate to conform with the shape of the artery to safely navigate through the artery with minimal trauma to the arterial walls.

Figure 4E:
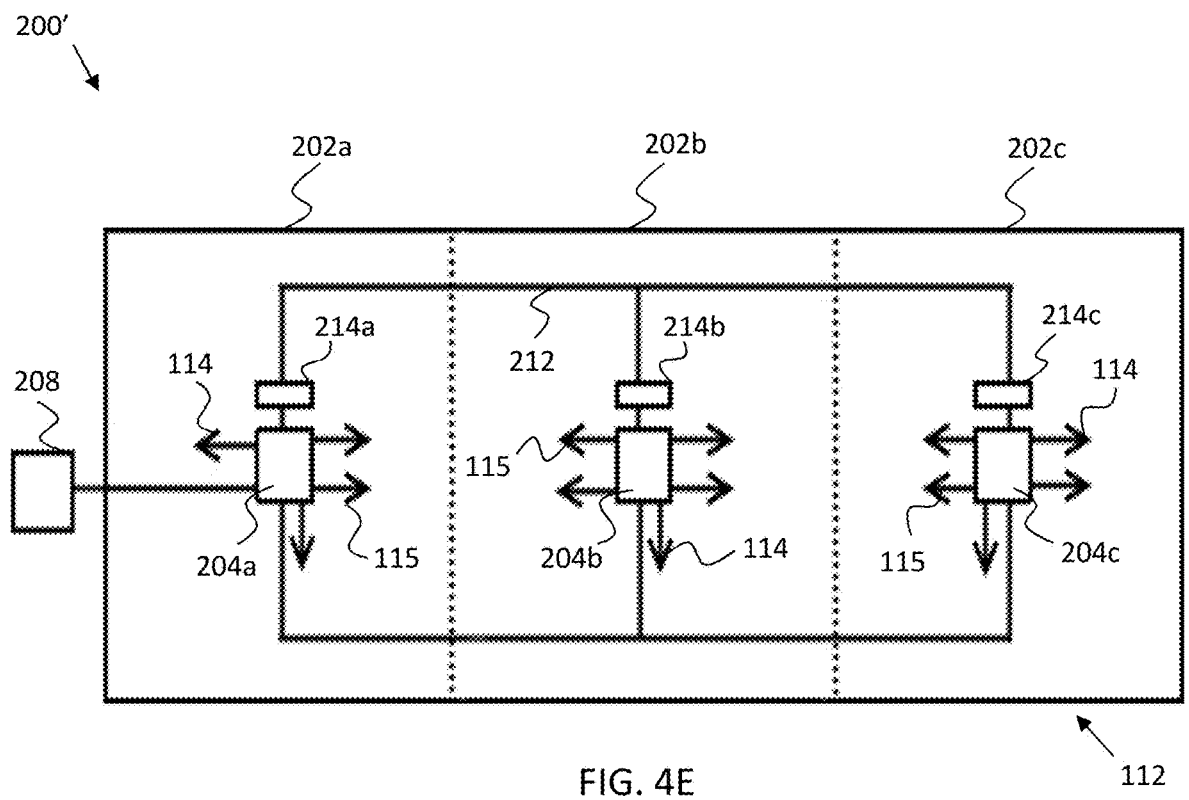
FIG. 4E illustrates a modified broadband control actuator system in accordance with embodiments of the invention.

In a specific inventive embodiment, with reference to FIG. 4E, a broadband control system 200' lacking a master controller 206 is shown. Here, the region controllers (204a, 204b, 204c) may communicate directly with one another. In this embodiment, control regions (202a, 202b, 202c) may be connected in reconfigurable distributed computational groups so as to facilitate functionality illustratively including parallel kinematic, serial kinematic, tactile data processing, acoustic, optical/visual, optoacoustic, or other signal processing, by way, in part, by the filters (214a, 214b, 214c). The computational groups being a combination of regions controllers (204a, 204b, 204c) in selective communication with one another (e.g., region controller 202a in communication with region controller 202c, but not region controller 202b). Each region controller (204a, 204b, 204c) may be configured to join specific channels, while maintaining a primary open channel, to coordinate with one another and form the computational groups. Therefore, different actuation link groups may be created between the control regions (202a, 202b, 202c). The communications may be handled by a 'group master'. The 'group master' being a region controller (204a, 204b, 204c) having primary control over a computational group and/or for forming specific groupings of the control regions (202a, 202b, 202c) similar to a master slave-chain configuration. Region controllers (204a, 204b, 204c) may be commanded to join an actuator link group (i.e., computational group) by being told to subscribe to a specific channel via the primary open channel. This eliminates the need for centrally coordinated process communications. In addition, each region controller (204a, 204b, 204c) may communicate over the communication medium (e.g., as the SMM body 112, a ground plane, a power plane, or other wired connection 212) directly for higher efficiency. It should be appreciated that the 'group master' may be interchangeable among the region controllers (204a, 204b, 204c) depending on a specific task. Furthermore, multiple 'group masters' may exist depending on the overall geometry of the SMM body 112 and/or the actuation complexity of particular regions of an SMM body 112.

Figure 5A:
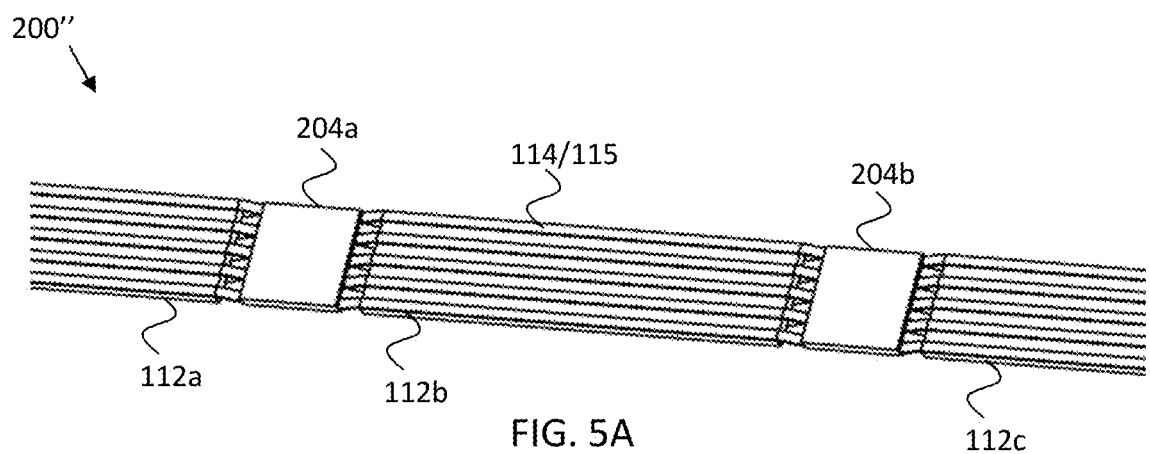
FIGS. 5A and 5B illustrate two or more controllers controlling two or more distinct and separated shape memory actuators in accordance with embodiments of the invention, where
Figure 5B:
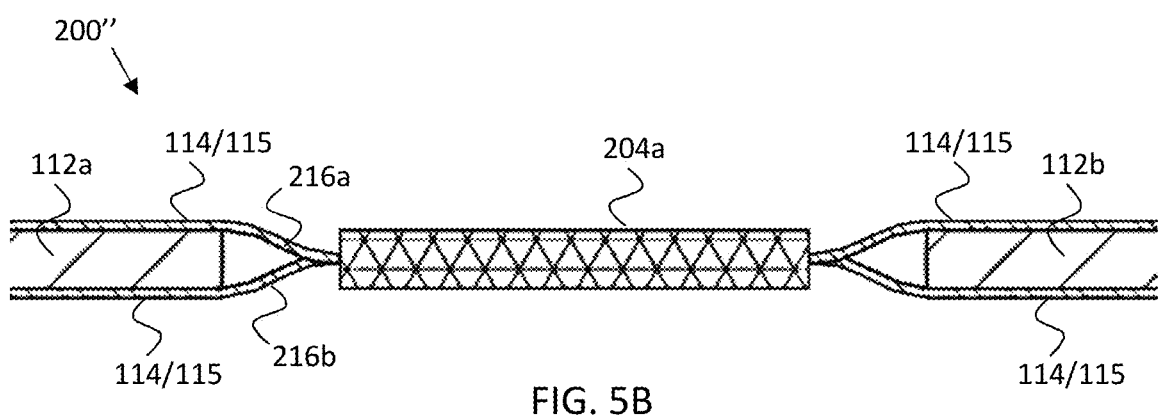

In a specific inventive embodiment, with reference to FIGS. 5A-5B, a broadband control system actuator 200" is shown having region controllers (204a, 204b) situated between two or more individual and distinct monolithic SMM bodies (112a, 112b, 112c). The broadband control system actuator 200" is configured to operate similar to the aforementioned broadband control system actuators (200, 200'), except the region controllers (204a, 204b) may control two or more individual SMM bodies (112a, 112b, 112c). FIG. 5B depicts a longitudinal cross-section view of a region controller 204a connected between two SMM bodies (112a, 112b) to further illustrate how a region controller 204a with alternating leads (216a, 216b) connects with conductors (114, 115) interfaced on a top and bottom surface of the SMM bodies (112a, 112b).

Structures—Tubular Shape Memory Actuators

Figure 6A:
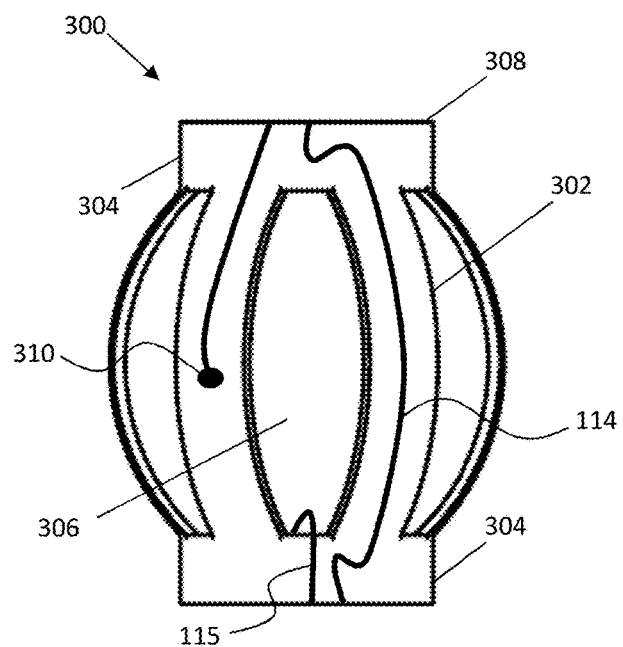
FIGS. 6A-6B illustrate a controllable tubular shape memory actuator having a plurality of bendable actuators in accordance with embodiments of the invention, where
Figure 6B:
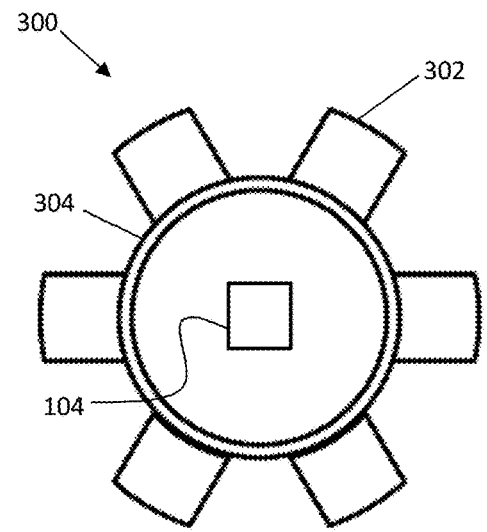

In specific inventive embodiments, with reference to FIG. 6A-6B, a tubular shape memory actuator 300 is shown, where FIG. 6A is a side view of the actuator 300 and FIG. 6B is a top view thereof. The tubular shape memory actuator 300 includes a plurality of individual bending actuators 302 radially spaced and integrally connected between two rings 304. The bending actuators 302 being made of SMM. The bending actuators 302 and rings 304 may be fabricated from a SMM monolithic structure, or connected using welding techniques (e.g., ultrasonic welding), brazing, soldering, adhesives, fasteners (e.g., screws, clamps, or rivets) and equivalents thereof.

The bending actuators 302 may be separated by a void 306, which may be used as an insulator to minimize crosstalk, and/or provide each individual actuator 302 with enough space to actuate.

The rings 304 may be used for a variety of purposes. A controller 104 may be housed concentrically within one or more of the rings 304. The rings 304 may provide additional space for individual conductor 114/115 tracing before/after traversing the bending actuators 302. The rings 304 may also provide an attachment point for other tubular shape memory actuators 300. For example, the end 308 of the ring 304 may have an interlocking mechanism for an end 308 of a second shape memory actuator 300, as further described below. Therefore, multiple tubular shape memory actuators 300 may be connected to form a multi-structured actuator, with shape memory actuator 300 being individually controlled, and/or controlled in unison by one or more controllers 104. It should be appreciated that the aforementioned control methods may be applied to control one or more tubular shape memory actuators 300.

In particular inventive embodiments, the tubular shape memory actuator 300 includes a plurality of individual conductors 114/115 interfaced with the bendable actuators 302 and/or rings 304. The conductors 114/115 are likewise physically separated by SMM to heat SMM situated between the conductors 114/115, as well as any SMM in the vicinity of the conductors (114, 115) as described above with reference to the pulse control methods. The voids 306 may advantageously provide one or more routes for conductors 114/115 to traverse to opposing surfaces of the bendable actuators 302 to improve the density of individual conductors 114/115. The conductors 114/115 may be interfaced with the individual actuators 302 so as to create conduction points 310 at specific locations along the individual actuators 302. For example, a conduction point 310 may be created at the center of the individual actuators 302, represented as point 310. It should be appreciated, that the conductors 114/115 may traverse the entire length of a bendable actuator(s) 302, only a portion of the individual actuator(s) 302, or multiple conductors 114/115 may be interfaced on a bendable actuator 302 to form multiple conduction points thereon.

Figure 6C:
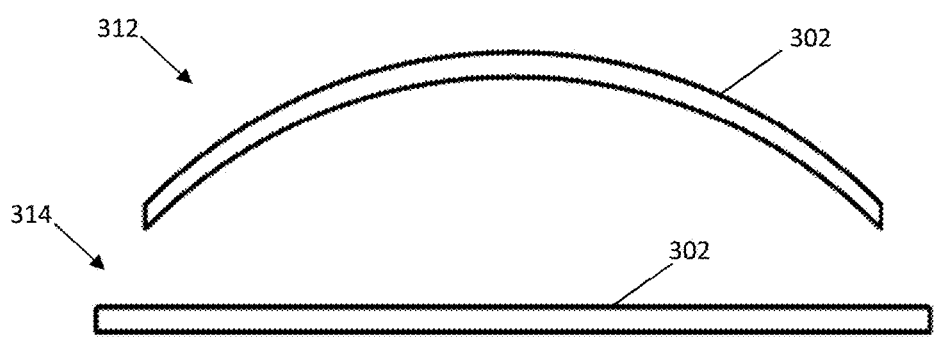
FIG. 6C illustrates an actuating motion of an individual actuator of the tubular shape memory actuator shown in FIGS. 6A-6B in accordance with embodiments of the invention.

Depending on the pre-treatment of the individual actuators 302 to a "memorized" state, each individual actuator 302 can therefore be actuated using the same control methods as described above. In a specific embodiment, with reference to FIG. 6C, a bendable actuator 302 may have a deformable configuration as shown at 312, and upon heating the SMM, for example at conduction point 310, a "memorized" configuration may be obtained as shown at 314. This may cause the tubular shape memory actuator 300 to bend in a first degree of freedom along a first axis. By controlling other bendable actuators 302, the shape memory actuator 300 may bend in a second degree of freedom along a second axis, and so forth. It should be apparent that the shape memory actuator 300 may also expand/contract its overall length depending on the control of a combination of bendable actuators 302.

Figure 7A:
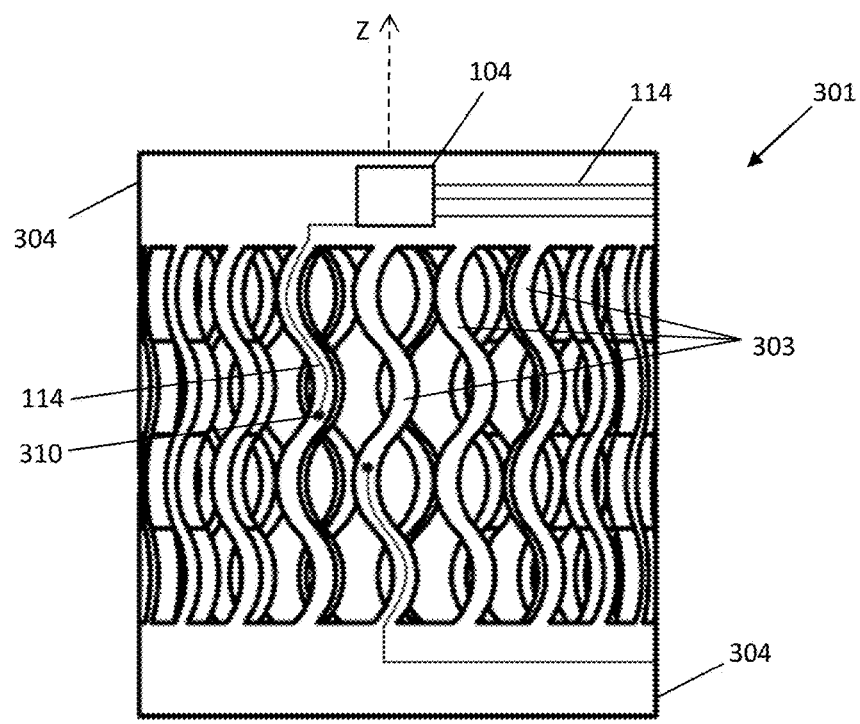
FIGS. 7A-7B illustrate a controllable tubular shape memory actuator having a plurality of in-line actuators in accordance with embodiments of the invention, where
Figure 7B:
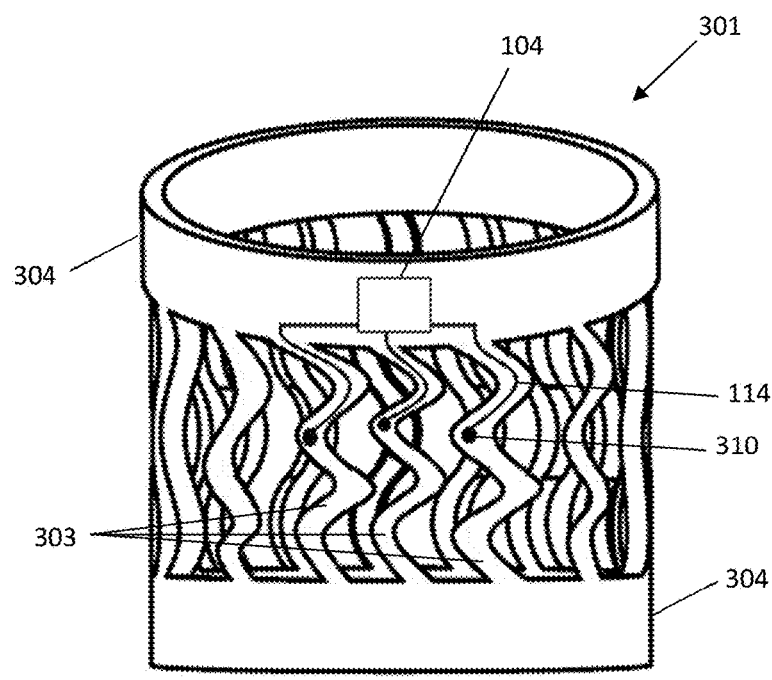

In specific inventive embodiments, with reference to FIGS. 7A-7B, a tubular shape memory actuator 301 having a plurality of in-line actuators 303 is shown, where FIG. 7A illustrates the actuator 300 in an unactuated configuration and FIG. 7B illustrates the actuator 300 having a portion of the plurality of in-line actuators 303 in an actuated configuration. The in-line actuators 303 are configured to actuate along a length of the in-line actuator 303 in a longitudinal and radial direction (as best seen in FIG. 7B), rather than bending inwardly toward the center of the rings 304 or outwardly away from the center of the rings 304 such as the actuation motion of the bendable actuators 302 shown in FIGS. 6A-6C. The in-line actuators 303 traverse between two rings 304 and are radially spaced about the rings 304. In a particular embodiment, each in-line actuation is sinusoidal in shape. When an in-line actuator 303 is activated, the length of the in-line actuator 303 decreases, essentially decreasing the 'wavelength' and increasing the 'amplitude' of the 'waves' of the sinusoidally shaped in-line actuator 303. Therefore, there is no mid-plane (i.e., a mid-plane being defined as a plane where if a Z-axis extends through the center of the tubular actuator 301, then a mid-plane is defined as a plane perpendicularly intersecting the in-line actuators 303 between the two rings 304 in the X-Y direction) change in diameter of the actuator 301. The in-line actuators 303 are particularly advantageous as the diameter of the tubular actuator 301 remains relatively unchanged compared to the bulging out, and mid-plane diameter change as seen with the bendable actuators 302 of the actuator 300 shown in FIGS. 6A-6C. This advantage is particularly relevant in an application where the tubular shape memory actuators (300, 301) are housed within a sheath, or where the tubular shape memory actuators (300, 301) act as a sheath or guide for some other device housed within the tubular shape memory actuator (300, 301). In this instance, the inward/outward actuation of the bendable actuators 302 shown in FIGS. 6A-6C may kink, pinch, or otherwise make inconsistent contact with the sheath during actuation, which may inhibit the actuators 300 movement or affect the overall stability of the actuator 300 in the sheath. On the other hand, the in-line actuation of the in-line actuators 303 preserves the overall shape (e.g., tube diameter) of the actuator 301 so as to remain concentric within the sheath and/or not make interfering contact with the sheath while being actuated.

The tubular shape memory actuator 301 having in-line actuators 303 may further include many of the same elements as the other actuators described above, such as a controller 104 and conductors (114, 115), and may operate by any of the aforementioned control methods.

Figure 8A:
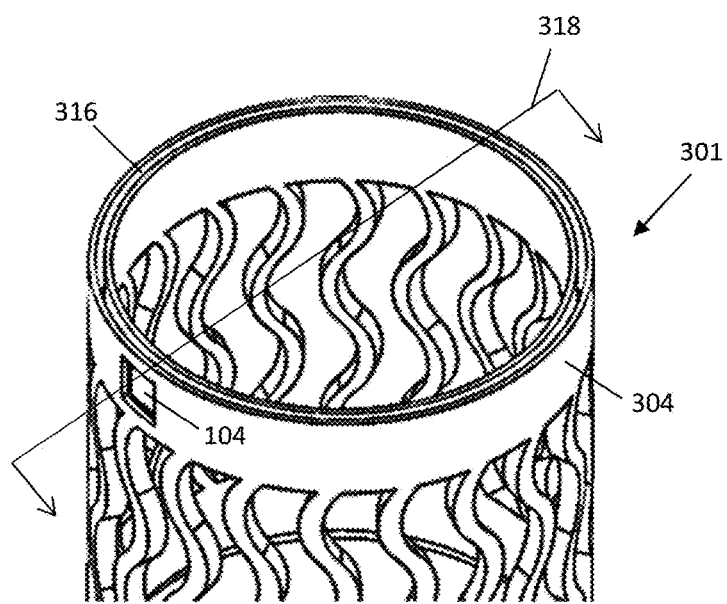
FIGS. 8A-8C illustrate a tubular shaped memory actuator with a controller embedded within a ring of the tubular shape memory actuator in accordance with embodiments of the invention.
Figure 8B:
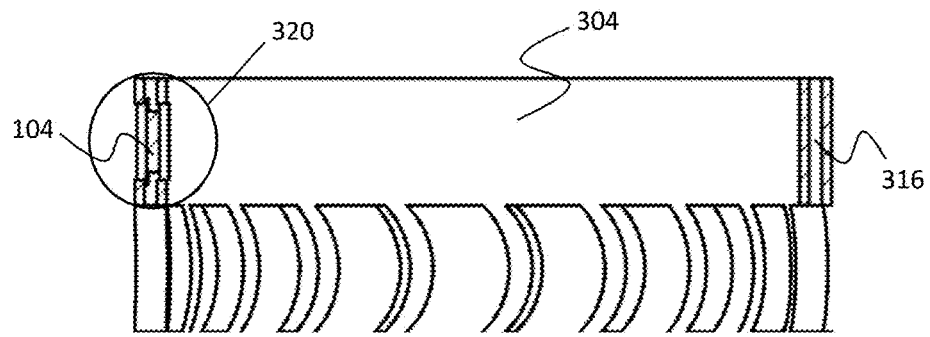
Figure 8C:
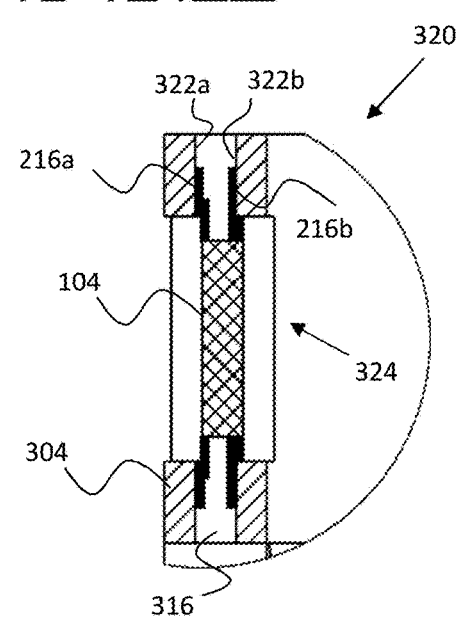

In a particular inventive embodiment, with reference to FIGS. 8A-8C, a tubular shape memory actuator 301 is shown having a controller 104 embedded within a ring 304 of the tubular shape memory actuator 301. FIG. 8A is a perspective view of a top portion of the actuator 301, FIG. 8B is a cross-sectional view along line 318 shown in FIG. 8A, and FIG. 8C is a detailed view of the circled region 320 shown in FIG. 8B. The controller 104 may attach/connect or integrate within a notch 316 formed within the material of the ring 304. As best shown in FIG. 8C, the notch forms two inner surfaces (322a, 322b) within the ring 304, where the controller 104 may have alternating leads (216a, 216b) that interface with these two inner surfaces (322a, 322b). The alternating leads (216a, 216b) may make direct contact with a portion of conductors (114, 115) traced on the inner surfaces (322a, 322b) to provide the control mechanisms of the actuators (302, 302') using any of the aforementioned control methods. A window 324 may further be formed through a portion of the ring 304 to receive the controller 104 therewithin for easy installation.

Figure 9A:
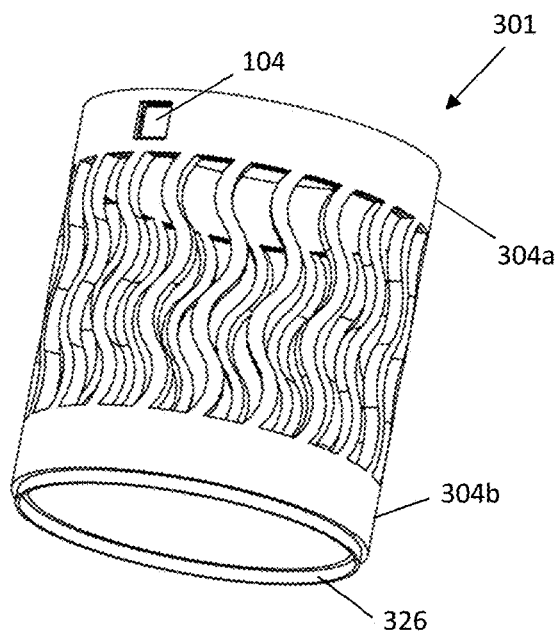
FIGS. 9A-9D illustrates a system and method for connecting two or more tubular shape memory actuators in accordance with embodiments of the invention, where
Figure 9B:
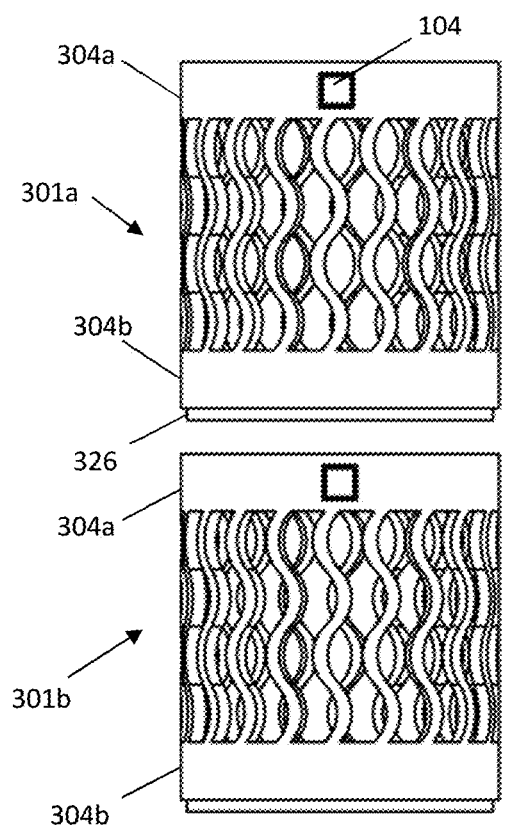
Figure 9C:
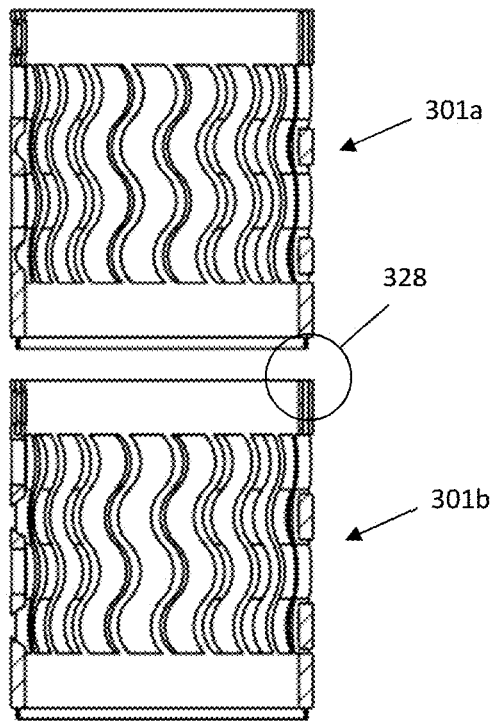
Figure 9D:
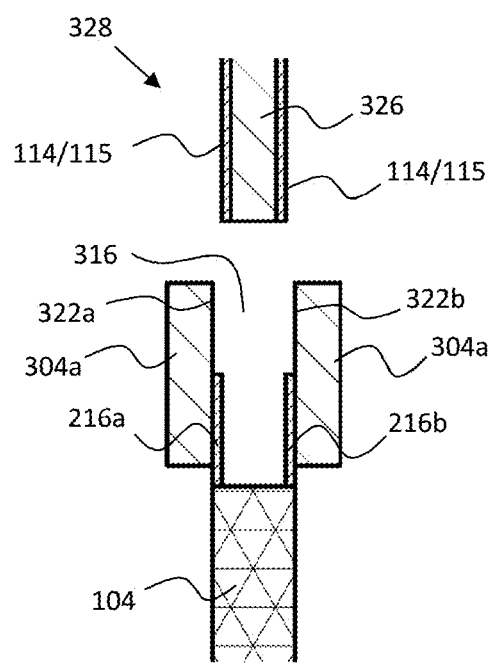

With reference to FIGS. 9A-9D, a system and method for connecting two or more tubular shape memory actuators (301a, 301b) is shown, where FIG. 9A is a perspective view of one actuator 301, FIG. 9B is a front view of two actuators (301a, 301b) to be connected, FIG. 9C is a longitudinal cross-section view of the two actuators (301a, 301b), and FIG. 9D is a detailed view of the circled region 328 shown in FIG. 9C. The tubular shape memory actuator 301 includes a first ring 304a having a notch 316 formed in the material of the first ring 304a, and a second ring 304b having a protrusion 326 extending from the bottom of the second ring 304b. The protrusion 326 is configured and formed to fit within the notch 316 formed on the first ring 304a as best seen in FIG. 9D to connect the two shape memory actuators (301a, 301b). The protrusion 326 may include conductors (114, 115) interfaced with opposing surfaces of the protrusion 326 to form an electrical connection with alternating controller leads (216a, 216b) interfaced with two inner surfaces (322a, 322b) formed by the notch 316 in the first ring 304a. It is contemplated that the connection between the tubular actuators (301a, 301b) may be further stabilized by a press-fit connection, snap-on snap-off clipping mechanism, soldering, adhesives, fastening elements, and equivalents thereof. In a particular embodiment, the electrical connection formed between the two tubular actuators (301a, 301b) permits the ability to control two or more tubular actuators (301a, 301b) with the broadband control system described above, although other control methods described herein may likewise control the tubular actuators (301a, 301b).

Figure 10A:
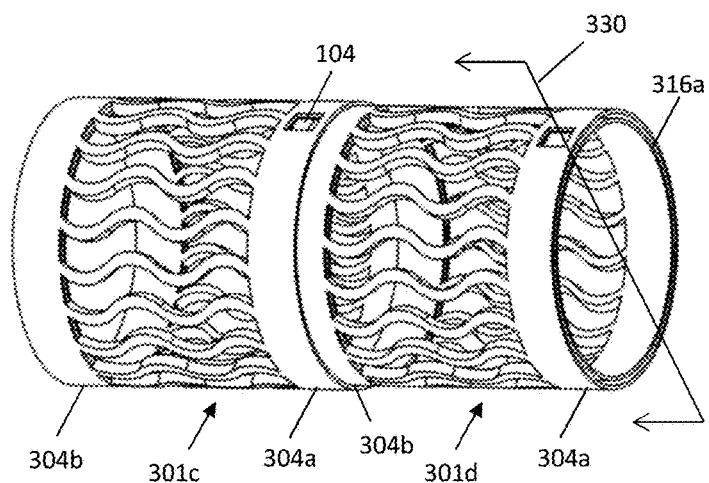
FIGS. 10A-10C illustrate a system and method for interlocking two or more tubular shape memory actuators in accordance with embodiments of the invention, where
Figure 10B:
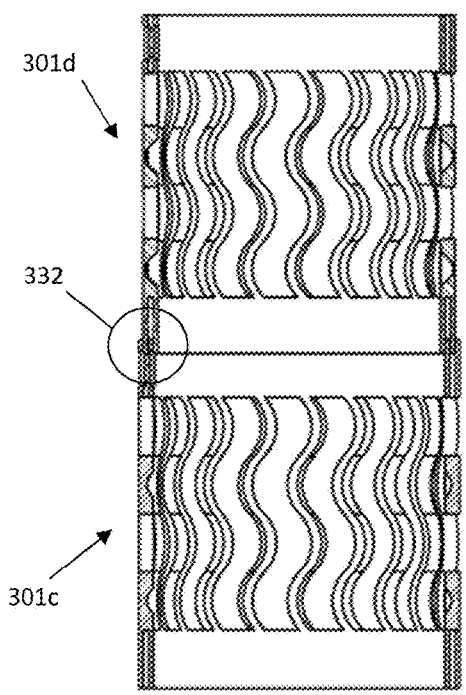
Figure 10C:
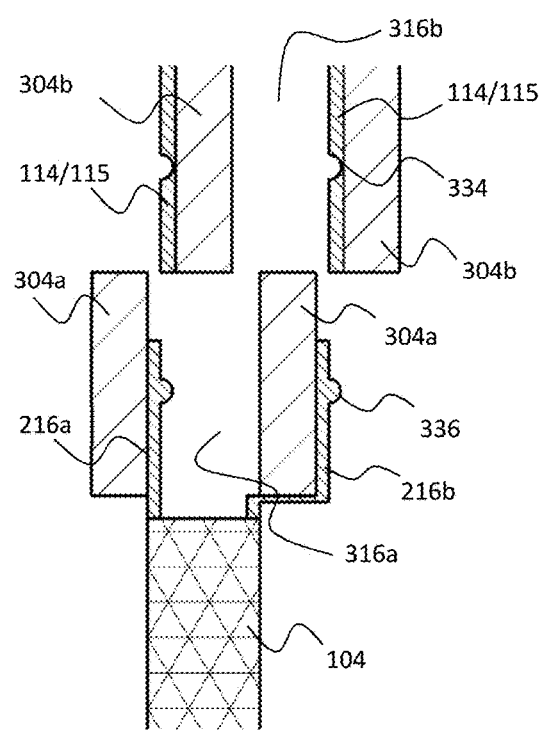

With reference to FIGS. 10A-10C, another embodiment of a system and method for interlocking two or more tubular shape memory actuators (301c, 301d) is shown, where FIG. 10A is a perspective view of two actuators (301c, 301d) connected, FIG. 10B is a cross-section view of the actuators (301c, 301d) along the line 330 shown in FIG. 10A, and FIG. 10C is a detailed view of the circled region 332 shown in FIG. 10B. The two or more tubular actuator (301c, 301d) include a first ring 304a having a first notch 316a and a second ring 304b having a second notch 316b. The diameter of the first notch 316a and the second notch 316b of a first tubular actuator 301c is greater than the diameter of the first notch 316a and the second notch 316b of a second tubular actuator 301d. The difference in the diameters allows a smaller diameter notch 316b of the second tubular actuator 301d, to interlock in a larger diameter notch 316a of the first tubular actuator 301c, as best seen in FIG. 10C. Conductors (114, 115) may interface with an outer surface and an inner surface the second notch 316b of the second tubular actuator 301d. Alternating lead wires (216a, 216b) may likewise interface with an outer surface and an inner surface of the first notch 316a of the first tubular actuator 301c to link and electrically connect with the conductors (114, 115) on the second tubular actuator 301d. A conductor (114, 115) and leads (216a, 216b) may have an interaction point to secure the electrical connection. For example, the interaction point may include a recess 334 located on the conductors (114, 115) that mate with a projection 336 located on the leads (216, 216b). A plurality of tubular actuators (301c, 301d) may be interlocked by this method and may be further stabilized by the mechanisms as described above with respect to FIGS. 9A-9D. In a particular inventive embodiment, the rings 304 are made of SMM and are hardened by heat-treating the rings 304 to a temperature between 300-500 degrees C., or higher. Recent research also suggests that lower temperature ranges may also be used to harden the SMM dependent on the SMM composition. Hardened rings 304 make it easier to form connections between two or more tubular actuators 301 and form a stiffer connection. At the same time, hardening of the SMM confers a super-elastic quality to the SMM, such that the rings 304 do not inhibit movement of a structure composed of a plurality of tubular actuators 301 and may elastically retain their original shape under non-loading/actuating conditions.

Figure 11A:
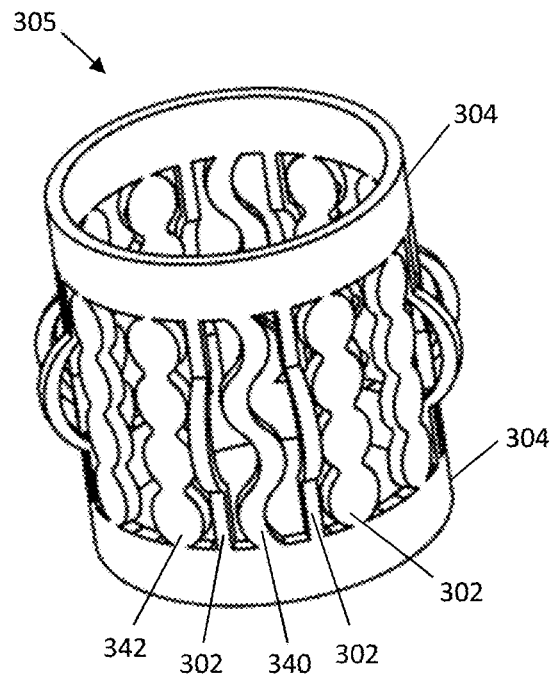
FIGS. 11A-11D illustrate a tubular shape memory actuator having load-balancing features and reinforcing features in accordance with embodiments of the invention, where
Figure 11B:
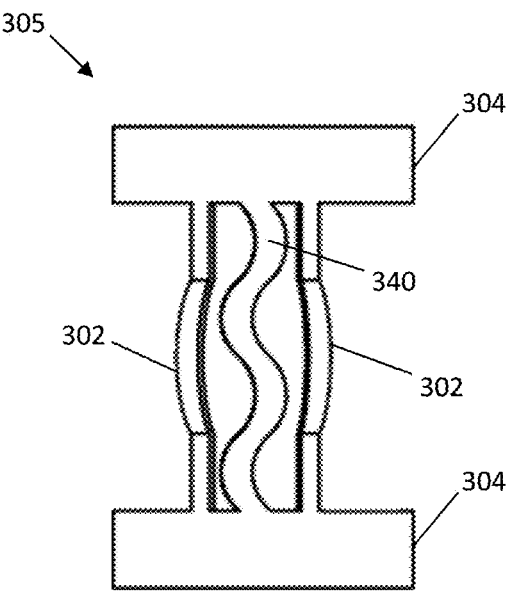
Figure 11C:
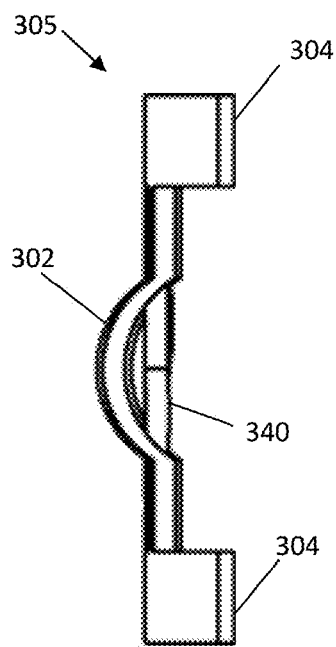
Figure 11D:
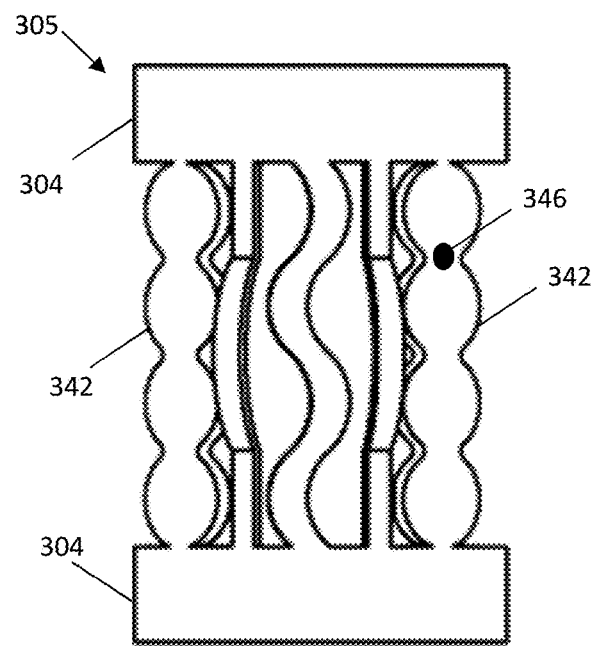

In specific inventive embodiments, with reference to FIGS. 11A-11D, a tubular shape memory actuator 305 is shown having load-balancing features 340 and reinforcing features 342, where FIG. 11A is perspective view thereof, FIG. 11B is a front view of an angular section thereof, FIG. 11C is a side view of the angular section thereof, and FIG. 11D is front view of a larger angular section thereof. The tubular shape memory actuator 305 includes a plurality of bendable actuators 302, a plurality of load-balancing features 340, and a plurality of reinforcing features 342. The bendable actuators 302, load-balancing features 340, and reinforcing features 342 all traverse between two rings 304 and are radially dispersed about the rings 304 in a particular configuration. In a particular configuration, load-balancing features 340 are radially positioned between two radially spaced bendable actuators 302, as best seen in FIG. 11B. The reinforcing features 342 are radially positioned adjacent to and on the outside of the bendable actuators 302, as best seen in FIG. 11D.

The load-balancing features 340 are configured to balance the load between two or more bendable actuators 302 to re-stabilize the tubular actuator 305 prior to and after an actuation event. The load balancing features 340 may be a passive spring made of SMM and heat-treated to harden the SMM. The passive spring may be in the form of a sinusoid to compress and expand similar to the aforementioned in-line actuators 303; however, the passive spring is not actively controlled. In a particular embodiment, the width or thickness of the passive spring may be twice the width or thickness of each bendable actuator 302 adjacent to the passive spring such that the passive spring may balance the load between the two bendable actuators 302 prior to, and after, an actuation event. For example, after an actuation event, the passive spring may either compress or expand the actuators 302 back to their original position once the bendable actuators 302 return to their deformable state.

The reinforcing features 342 are configured to reinforce, stabilize, and/or passively control the movement of the tubular actuator 305 between the two rings 304. The reinforcing features 342 may be struts made of SMM, or other materials, to aid in controlling the stiffness and flexure of the tubular actuator 305. The struts may have regions alternating in width creating pinch points 346, or flexion points, which forces the tubular actuator 305 to behave in a particular manner. The reinforcing features 342 may be particularly advantageous in applications where the tubular actuator 305 may experience heavy external loads, needs to impose loads on other objects, or needs to maintain a particular configuration more rigidly while still being capable of actuating in one or more axes.

In other inventive embodiments, the reinforcing features 342 are positioned in the midst of or anywhere within any SMA geometry, such as an SMA having a complex set of geometries, to reinforce, stabilize, and/or passively control the movement of the SMA. The reinforcing features 342 may be particularly adapted for SMA designs which are monolithic in nature and lack connection bands or rings 304. In addition, the reinforcing features 342 may be incorporated with non-tubular configurations of SMA including flat SMA designs, auxetic structures as described below, or a 3-D printed trellis king of matrix.

Structures—Layering

In specific inventive embodiments, with reference to FIGS. 12A-12E, a system and method for assembling or manufacturing a shape memory actuator 400 is shown, where FIG. 12A is an exploded top perspective view of the shape memory actuator 400, FIG. 12B is an exploded bottom perspective view thereof, FIG. 12C is an assembled top view of the shape memory actuator 400 shown with hidden lines, FIG. 12D is a cross section view thereof taken along line 416 shown in FIG. 12C, and FIG. 12E is a cross section view thereof taken along line 418 shown in FIG. 12C. The shape memory actuator 400 generally includes an SMM body 112, an insulation layer 402, a plurality of conductors (114, 115), and a sealant layer 406. The insulation layer 402 is configured to provide insulation and/or reduce cross-talk between conduction points. The insulation layer 402 may be made of a laminate, a ceramic, a film, vapor deposited particles, epoxies, silicone, and any other non-conductive materials. The insulation layer 402 further includes conduction holes 408 and sealant holes 410. The conduction holes 408 permit portions of a conductor (114, 115) to interface directly with the SMM body 112 at desired conduction points, or sections, of the SMM body 112. The sealant holes 410 are configured to permit a sealant to interface and anchor directly to the SMM body 112 to ensure the sealant layer 406, conductors (114, 115), insulation layer 402, and SMM body 112 are securely assembled together. For example, as best seen by comparing FIG. 12D and FIG. 12E, portions of each conductor (114, 115) only interface with the SMM body 112 through the conduction holes 408 as seen in FIG. 12D and are otherwise insulated from the SMM body 112 as seen in FIG. 12E. Likewise, the sealant only anchors to the SMM body 112 through the sealant holes 410 as seen in FIG. 12E and otherwise interface with the insulation layer 402 as seen in FIG. 12D. The sealant may be made of a natural or synthetic flexible and/or semi-rigid material appropriate to the desired target environment including elastomers, thermoplastics, and thermosets that illustratively include rubbers, epoxies, silicones, block co-polymers, latex, polyvinyl chloride, nitrile rubber, neoprene, and combinations thereof.

Figure 13A:
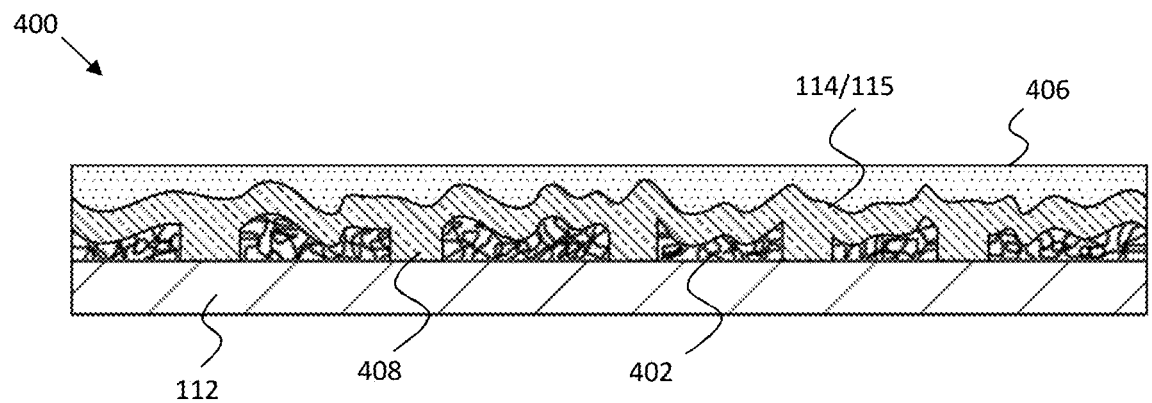
FIGS. 13A-13B illustrate a shape memory actuator having an insulating graphene oxide layer in accordance with embodiments of the invention, where
Figure 13B:
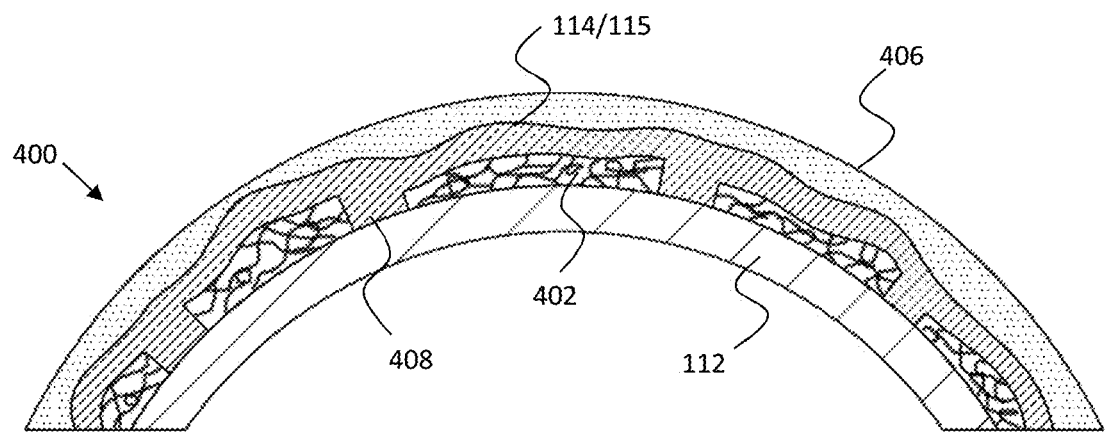

In particular inventive embodiments, with reference to FIGS. 13A-13B, the insulation layer 402 may be made of a carbonaceous material of graphene oxide, graphene nano-platelets, a carbon aerogel, carbon sponge like material, carbon nano-tubes, or turbostratic carbon for several reasons. For one, carbonaceous material has low conductivity to act as an insulator. Secondly, the carbonaceous material may further be assembled, adhered, or deposited on the SMM body 112 to have a micro-structure that provides a flexible buffer between the conductors (114, 115) and the SMM body 112. The flexible buffer is configured to create a highly irregular surface on which the conductors (114, 115) will interface thereon. The advantage being that the overall surface area and volume of conductive material is increased to account for any stretching of the SMM body 112 experiences when the SMM body 112 is actuated as seen in FIG. 13B. In a specific inventive embodiment, the carbonaceous material may be in the form of several particulates that loosely associate to create this flexible buffer affect. In a specific inventive embodiment, the carbonaceous material may be in a liquid or paste-like form that may harden to create an expandable/contractable semi-flexible web of graphene oxide.

Structures—Auxetics

Figure 14A:
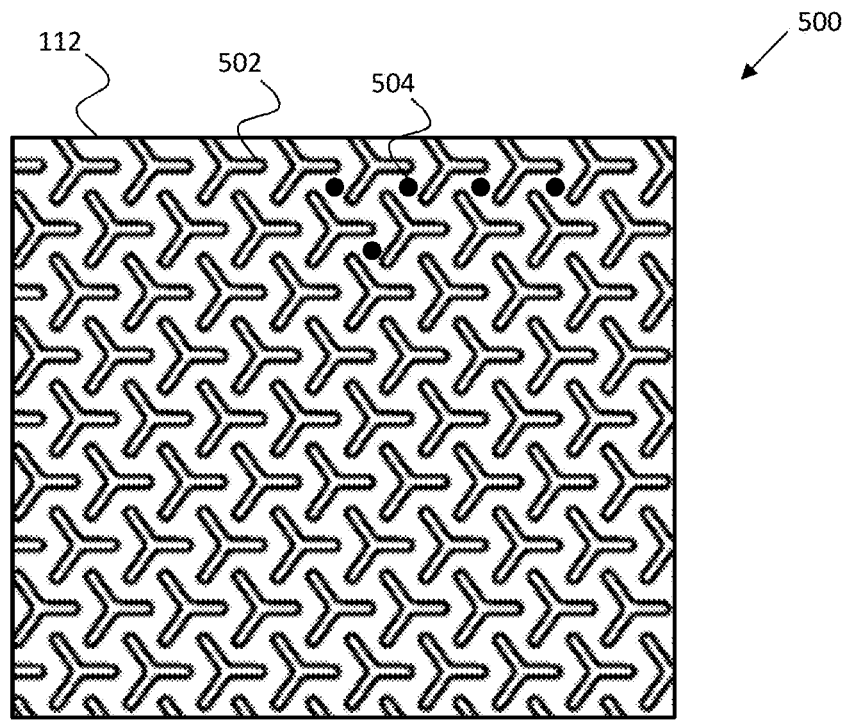
FIGS. 14A-14B illustrate an auxetic shape memory actuator in accordance with embodiments of the invention, where
Figure 14B:
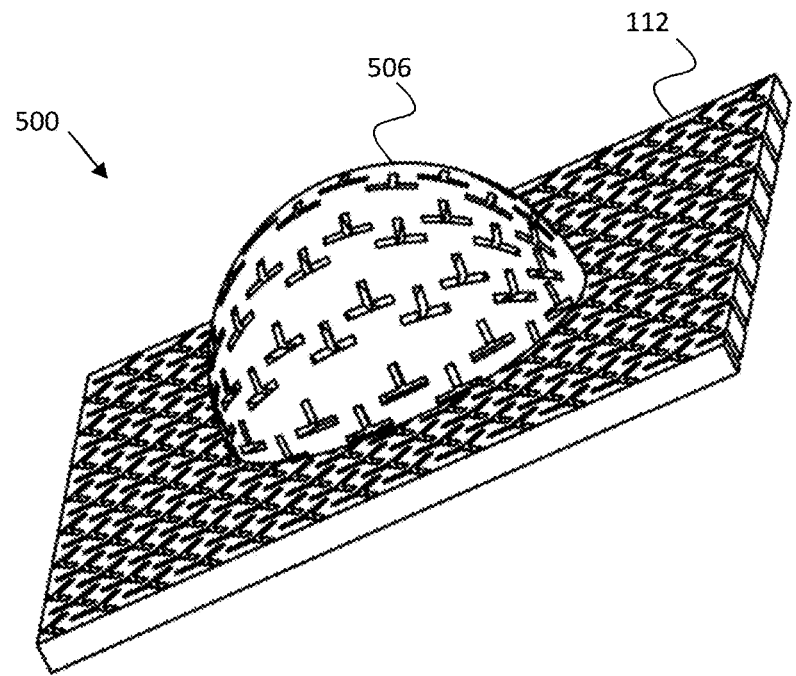

In specific inventive embodiments, with reference to FIGS. 14A-14B, an auxetic shape memory actuator 500 is shown, where FIG. 14A is a top view of the actuator 500 in an unactuated state, and FIG. 14B is perspective view thereof in an actuated state. The auxetic shape memory actuator 500 is configured to form three-dimensional (3-D) shapes starting from a 2-D planar structure or sheet. In general, auxetic materials have a negative Poisson ratio, in that the material expands perpendicularly to a direction of an applied load. In addition, the internal shape or structure of an auxetic material increases the number of available actuation axes and shape formation, in which an auxetic shape memory actuator 500 may be folded like origami to form very complex 3-D shapes or simply expand to increase the area of a locality that creates a 3-D deformation. In one embodiment, the auxetic shape memory actuator 500 includes an SMM body 112 having an auxetic internal structure. The auxetic internal structure may include a plurality of three-pronged voids 502 patterned in an alternating fashion in the SMM body 112 as shown in FIG. 14A. It should be appreciated that other auxetic internal structures of the SMM body 112 may exist including the structures identified by Korner, Carolin, and Yvonne Liebold-Riveiro. "A systematic approach to identify cellular auxetic materials." *Smart Materials and Structures* 24.2 (2014): 025013, which is incorporated by reference herein in its entirety. Between the voids 502, conductors (114, 115) are traced to form conduction points 504 as described above. FIG. 14B illustrates a 3-D hemisphere formed by the actuator 500. One will appreciate that the systems and control methods described herein and used in conjunction with auxetic structures presents the ability to form very intricate 3-D structures for a variety of applications.

Peripherals

Particular inventive embodiments of the SMA further include peripherals interfaced directly to the material and accessible and/or controlled by the controllers or control array using any of the control or data signaling schemes described herein (e.g., multi-band analog, digital, or by direct connection to the controller via a conductor). The peripherals may illustratively include light emitting diodes (LEDs), cameras, monitors/displays, sensors, actuators/motors, the internet, a local area network, a computer having machine learning capabilities, as well as other devices. In a specific embodiment, a piezoelectric actuator may be assembled between a power conductor and ground conductor to provide actuation along a particular axis when subjected to an electrical load via the controller methods described herein. The piezo actuator may act as a spring to return a portion of the SMM body back to an original state after removing a heat source. The piezo actuator may act as mechanism of motion to "walk", expand, contract, raise, lower, or otherwise move the SMM body to a new position or orientation.

Example—SMA Design with Multiple Degrees of Freedom

Figure 15A:
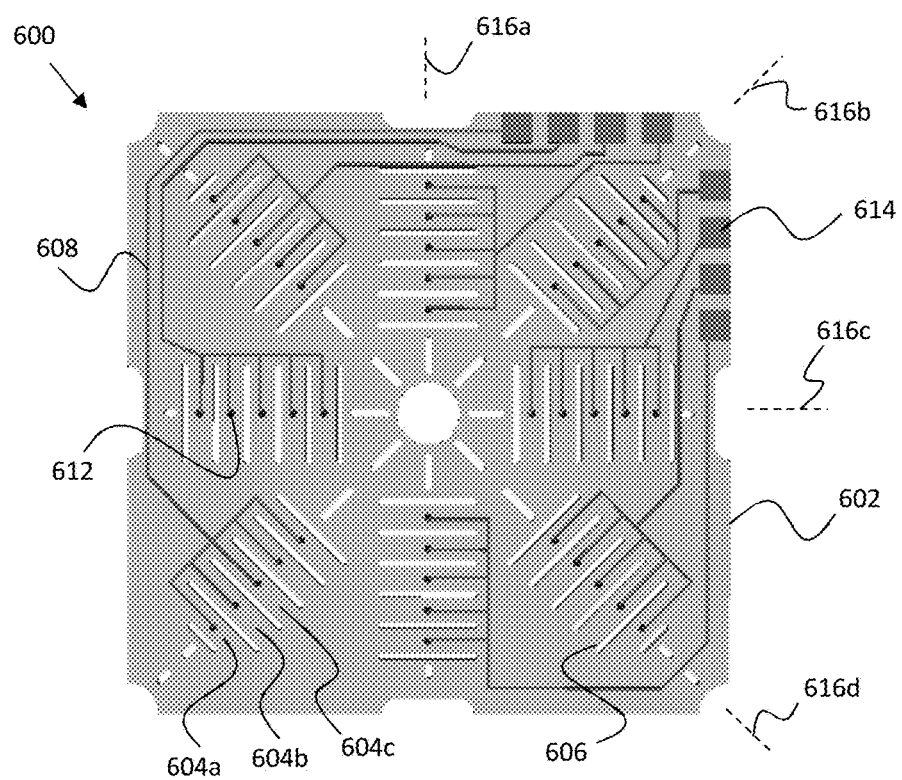
FIGS. 15A-15B illustrate an example of a shape memory actuator having multiple degrees of freedom in accordance with embodiments of the invention, where
Figure 15B:
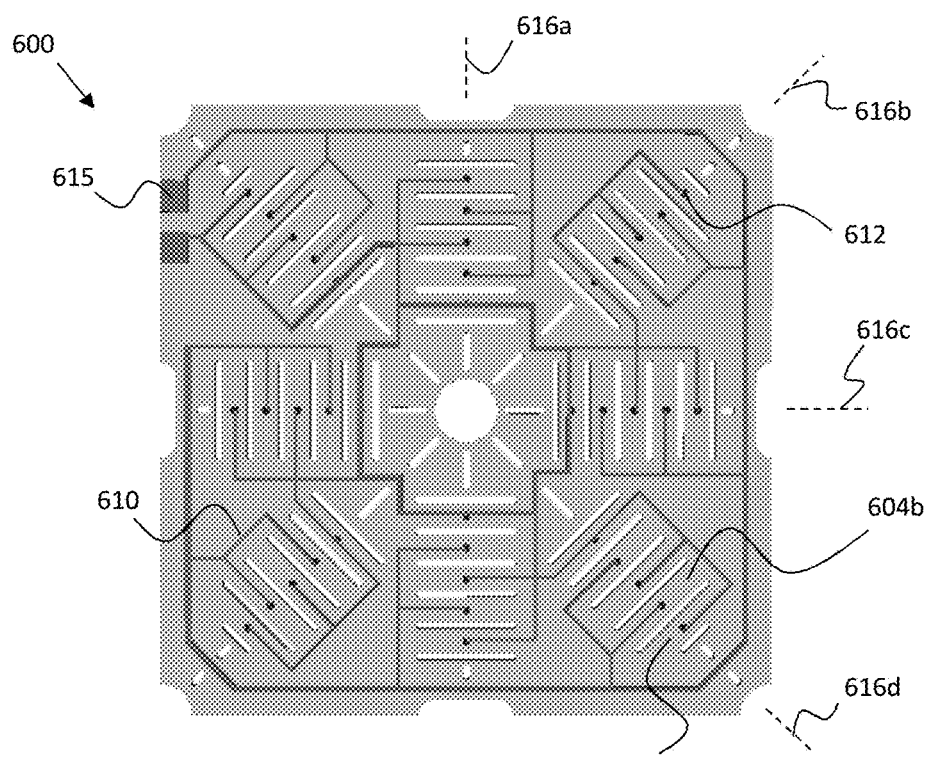

With reference to FIGS. 15A and 15B, an example of an SMA 600 having multiple degrees of freedom is shown, where FIG. 15A is a front view of the SMA 600, and FIG. 15B is a back view thereof. The SMA 600 generally includes an SMM body 602 having a plurality of individual actuation sections (604a, 604b, 604c) each separated by a small insulation gap 606. Power conductors 608 and ground conductors are traced on a front surface and back surface of the SMM body 602, respectively, to create conduction points 612 positioned at the center of each actuation section (604a, 604b, 604c). The SMA 600 further includes controller connection points (614, 615) to connect controller leads with the conductors (608, 610) to facilitate control of the SMA 600 using any of the control schemes described herein.

The actuation sections (604a, 604b, 604c) are grouped in a linear fashion along different actuation axes (616a, 616b, 616c, 616d). As shown in FIGS. 15A and 15B, the groups of actuation sections (604a, 604b, 604c) are radially positioned about the SMM body 602 to form four actuation axes (616a, 616b, 616c, 616d) about which the SMM body 602 may bend either into the page or out of the page based on which actuation sections (604a, 604b, 604c) are activated using the control and ohmic heating methods described above. This is accomplished based on the 'memorized' state of each actuation section (604a, 604b, 604c). In particular, within a group of actuation sections (604a, 604b, 604c), alternating actuation sections, such as section 604a and 604c, are 'memorized' to bend into the page, while the adjacent actuation sections 604b are 'memorized' to bend out of the page. Therefore, for example, by heating actuation sections 604a and 604c causes the SMM body 112 to bend into the page about axis 616b. Likewise, heating actuation section 604b causes the SMM body 112 to bend out of the page about axis 616b. The same may be applied to the other groupings of actuation sections (604a, 604b, 604c) radially positioned about the SMM body 602 to control multiple degrees of freedom of the SMA 600.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A shape memory actuator system, comprising:
a shape memory actuator having a body made of a shape memory material (SMM), with a plurality of individual power conductors interfaced with a first portion of the body, and one or more individual ground conductors interfaced with a second portion of the body;
a power source for providing power to the plurality of individual power conductors; and
a pulse controller for controlling a frequency of current pulses between one or more of the plurality of individual power conductors and the one or more ground conductors, wherein the pulse controller imparts a partial or step-wise shape memory effect to a specific section of the body by pulsing current between a single power conductor and a ground conductor located at the specific section of the body with the proviso that the pulsed current only flows through the portion of SMM physically separating the single power conductor from the ground conductor.

2. The shape memory actuator system of claim 1 wherein the step-wise shape memory effect results from partial or incremental actuation of a specific section of the body made of SMM through partial incremental ohmic heating.

3. The shape memory actuator system of claim 1 wherein the plurality of individual power conductors are interfaced on an obverse side the body and the one or more of individual ground conductors are interfaced on a reverse side of the body.

4. The shape memory actuator system of claim 3 wherein the pulsed current flows perpendicularly through the portion of SMM physically separating the single power conductor on the obverse side of the body from the ground conductor on the reverse side of the body.

5. The shape memory actuator system of claim 1 wherein the single power conductor and the ground conductor are both on an observe side to the SMM body.

6. A shape memory actuator system, comprising:
a shape memory actuator having a body made of a shape memory material (SMM) partitioned into two or more discrete control regions, each control region having a plurality of individual power conductors interfaced with a first portion of the control region, and one or more individual ground conductors interfaced with a second portion of the control region;
a power source for providing power to the plurality of individual power conductors; and
at least two region controllers, wherein each region controller is positioned in a discrete control region for controlling a resistive heating current connection within their control region sufficient to impart shape memory between one or more of the plurality of individual power conductors and the one or more individual ground conductors with the proviso that each individual ground conductor is physically separated from each individual power conductor by a portion of SMM to permit current to flow through and ohmically heat said portion of SMM.

7. The shape memory actuator system of claim 6 wherein each region controller is mounted directly on a surface of the body of the SMM with at least one of fastening elements, adhesives, or I/O pin connections that make direct contact with the power conductors.

8. The shape memory actuator system of claim 6 wherein each region controller is embedded within the SMM body, or fit within a piece of removed SMM from the SMM body.

9. The shape memory actuator system of claim 8 wherein each region controller further comprises alternating leads which interface with two separate surfaces where a first lead is bent in a first direction, while an adjacent lead is bent in an opposing direction.

10. The shape memory actuator system of claim 6 further comprising a master controller connected to the power source, where the master controller sends a multichannel parallel signal to the region controllers to coordinate actuations and movements of the SMM body as a whole or at least part of a whole, where the actuations span over several of the two or more control regions or particular combinations of the two or more control regions.

11. The shape memory actuator system of claim 10 wherein each of the region controllers further comprise one or more discreet hardware notch filters or software notch filters that enables each region controller to discriminate, filter, and process the multichannel parallel signal for each region controller.

12. The shape memory actuator system of claim 11 wherein the one or more discreet hardware notch filters or the software notch filters further comprise TEO filters, demodulators, demultiplexers, low-pass filters, high-pass filters, and band-pass filters.

13. The shape memory actuator system of claim 10 wherein the multichannel parallel signal is embedded in the plurality of individual power conductors to provide both power and control commands to each region controller.

14. The shape memory actuator system of claim 10 wherein the multichannel parallel signal is embedded in the plurality of individual power conductors using at least one of an X10 industry standard protocol, a custom protocol, or an Ethernet protocol, to provide both power and control commands to each region controller.

15. The shape memory actuator system of claim 10 wherein the multichannel parallel signal is modulated or multiplexed.

16. The shape memory actuator system of claim 10 wherein the master controller and control regions are interconnected by serial or parallel digital communications.

17. The shape memory actuator system of claim 10 wherein the master controller is in communication with an electromagnetic tracking system or real-time x-rays/fluoroscopy that provides positional information of the SMM body.

18. The shape memory actuator system of claim 17 wherein the actuator system is used for traversal of arterial passages.

19. The shape memory actuator system of claim 17 wherein the master controller contains information as to a geometry and a location of each control region with respect to one another so as to activate and configure specific sections of the control regions.

20. The shape memory actuator system of claim 6 wherein each of the region controllers communicate directly with one another.

21. The shape memory actuator system of claim 20 wherein the control regions are connected in reconfigurable distributed computational groups so as to facilitate parallel kinematic functionality.

22. The shape memory actuator system of claim 21 wherein the computational groups are a combination of region controllers in selective communication with one another; and
   wherein each region controller is configured to join specific channels, while maintaining a primary open channel, to coordinate with one another and form the computational groups.

23. The shape memory actuator system of claim 6 wherein the shape memory actuator has a tubular shape formed with a plurality of individual bending actuators radially spaced and integrally connected between a set of two rings.

24. The shape memory actuator system of claim 23 wherein the bending actuators and the rings are fabricated from a SMM monolithic structure, or connected using welding techniques, brazing, soldering, adhesives, and fasteners.

25. The shape memory actuator system of claim 23 wherein one or more of the rings houses at least one region controller that is electrically connected to the plurality of individual power conductors and the one or more individual ground conductors that traverse bending actuators.

26. The shape memory actuator system of claim 23 wherein one or more of the rings provide an attachment point for one or more additional tubular shape memory actuators that forms a multi-structured actuator, with shape memory actuators being individually controlled, or controlled in unison by one or more controllers.

27. The shape memory actuator system of claim 23 wherein the plurality of individual bending actuators are sinusoidally shaped.

28. The shape memory actuator system of claim 23 further comprising load-balancing features and reinforcing features that are radially dispersed about the set of two rings.

29. An auxetic shape memory actuator configured to form three-dimensional (3-D) shapes starting from a 2-D planar structure or sheet formed from an SMM body having an auxetic internal structure, and further comprising:
   an SMM body having an auxetic internal structure;
   a plurality of individual power conductors interfaced with a first portion of the SMM body, and one or more individual ground conductors interfaced with a second portion of the SMM body;
   a power source for providing power to the plurality of individual power conductors; and
   a controller for controlling a resistive heating current connection sufficient to impart shape memory between the one or more of the plurality of individual power conductors and the one or more individual ground conductors with the proviso that the one or more individual ground conductors are physically separated from the plurality of individual power conductors.

* * * * *